(12) United States Patent
Lim et al.

(10) Patent No.: US 8,889,270 B2
(45) Date of Patent: Nov. 18, 2014

(54) ORGANIC LIGHT-EMITTING DEVICE

(75) Inventors: Jin-O Lim, Yongin (KR); Seok-Hwan Hwang, Yongin (KR); Young-Kook Kim, Yongin (KR); Hye-Jin Jung, Yongin (KR); Sang-Hyun Han, Yongin (KR); Yoon-Hyun Kwak, Yongin (KR); Sun-Young Lee, Yongin (KR); Chang-Ho Lee, Yongin (KR); Hee-Joo Ko, Yongin (KR); Jong-Hyuk Lee, Yongin (KR); Sung-Chul Kim, Yongin (KR)

(73) Assignee: Samsung Display Co., Ltd., Yongin-si (KR)

(*) Notice: Subject to any disclaimer, the term of this patent is extended or adjusted under 35 U.S.C. 154(b) by 186 days.

(21) Appl. No.: 13/290,046

(22) Filed: Nov. 4, 2011

(65) Prior Publication Data
US 2012/0267613 A1   Oct. 25, 2012

(30) Foreign Application Priority Data
Apr. 22, 2011   (KR) .................. 10-2011-0037980

(51) Int. Cl.
*H01L 51/50*   (2006.01)
*C07D 471/22*   (2006.01)
*H01L 51/00*   (2006.01)

(52) U.S. Cl.
CPC ......... *H01L 51/0072* (2013.01); *H01L 51/0085* (2013.01); *H01L 51/5072* (2013.01); *H01L 51/5016* (2013.01); *C07D 471/22* (2013.01); *H01L 51/5012* (2013.01); *H01L 51/0061* (2013.01); *H01L 51/0064* (2013.01); *H01L 51/5056* (2013.01)
USPC ................ 428/690; 546/32; 585/26; 549/456

(58) Field of Classification Search
None
See application file for complete search history.

(56) References Cited

U.S. PATENT DOCUMENTS

| | | |
|---|---|---|
| 5,635,308 A | 6/1997 | Inoue et al. |
| 5,645,948 A | 7/1997 | Shi et al. |
| 5,972,247 A | 10/1999 | Shi et al. |
| 6,465,115 B2 | 10/2002 | Shi et al. |
| 6,596,415 B2 | 7/2003 | Shi et al. |
| 2006/0210830 A1 | 9/2006 | Funahashi et al. |
| 2007/0155991 A1 | 7/2007 | Funahashi |
| 2008/0306303 A1 | 12/2008 | Rostovtsev et al. |
| 2010/0127618 A1 | 5/2010 | Ohrui et al. |
| 2012/0097929 A1* | 4/2012 | Kim et al. .................. 257/40 |

FOREIGN PATENT DOCUMENTS

| | | | |
|---|---|---|---|
| JP | 8-12600 | 1/1996 | |
| JP | 2000-3782 | 1/2000 | |
| JP | 2006-66580 A | 3/2006 | |
| JP | 2008-290999 A | 12/2008 | |
| WO | WO 2008/150872 A1 | 12/2008 | |
| WO | WO-2011/037429 A2 * | 3/2011 | ............. C09K 11/06 |

OTHER PUBLICATIONS

Machine English translation of WO 2011/037429 A2. Mar. 14, 2014.*
Tang, et al. "Organic electroluminescent diodes", Appl. Phys. Lett. vol. 51, No. 12, Sep. 21, 1987, pp. 913-915.
Sakamoto, et al., "Synthesis, Characterization, and Electron-Transport Property of Perfluorinated Phenylene Dendrimers", Journal American Chemical Society, 2000, vol. 122, pp. 1832-1833.
Yamaguchi, et al., "Diphenylamino-Substituted, 2,5-Diarylsiloles for Single-Layer Organic Electroluminescent Devices", The Chemical Society of Japan, Chemistry Letters 2001, received Nov. 10, 2000, pp. 98-99.
Adachi, et al., "Confinement of charge carriers and molecular excitons within 5-nm-thick emitter layer in organic electroluminescent devices with a double heterostructure", Appl. Phys. Lett. vol. 57, No. 6, Aug. 6, 1990, pp. 531-533.

* cited by examiner

Primary Examiner — J. L. Yang
(74) Attorney, Agent, or Firm — Christie, Parker & Hale, LLP

(57) ABSTRACT

A heterocyclic compound represented by Formula 1 below and an organic light-emitting device including the heterocyclic compound:

Formula 1

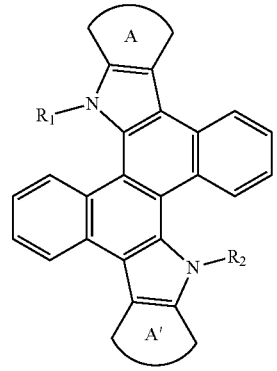

wherein $R_1$ and $R_2$, and A and A' are defined as in the specification.

20 Claims, 1 Drawing Sheet

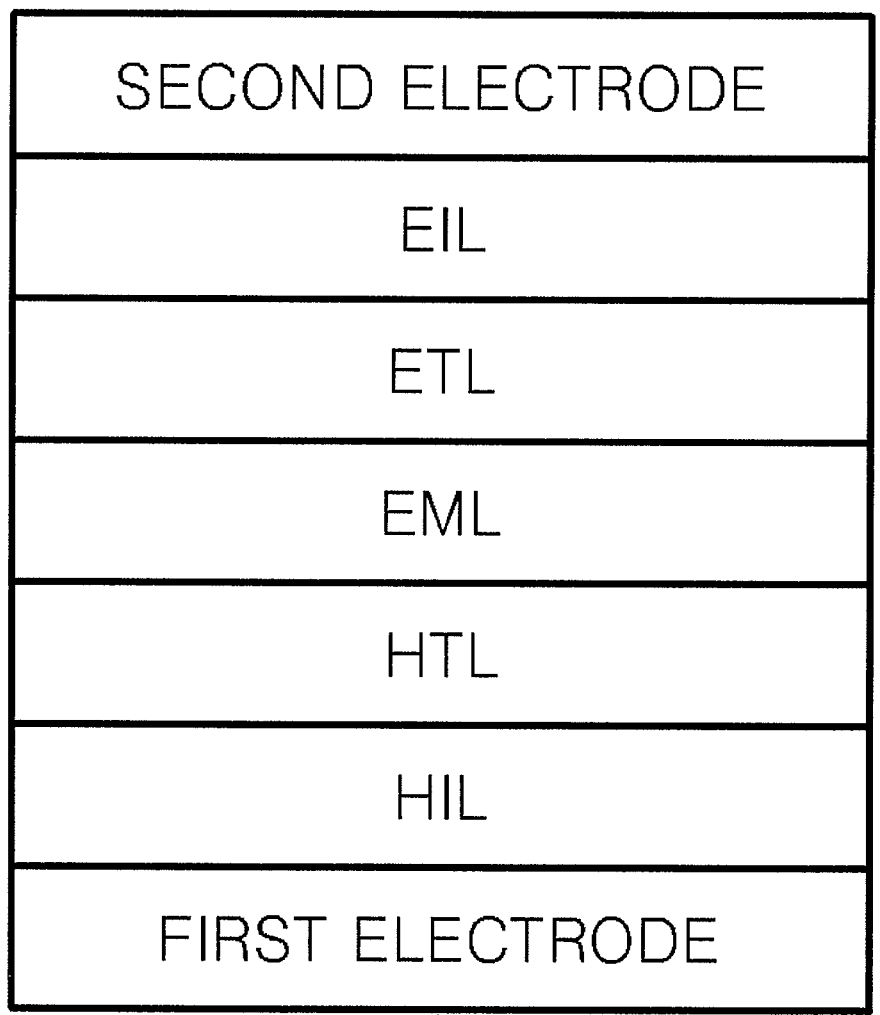

ORGANIC LIGHT-EMITTING DEVICE

CROSS-REFERENCE TO RELATED PATENT APPLICATION

This application claims the benefit of Korean Patent Application No. 10-2011-0037980, filed on Apr. 22, 2011, in the Korean Intellectual Property Office, the entire content of which is incorporated herein by reference.

BACKGROUND

1. Field

The following description relates to a heterocyclic compound represented by Formula 1 and an organic light-emitting device including the heterocyclic compound.

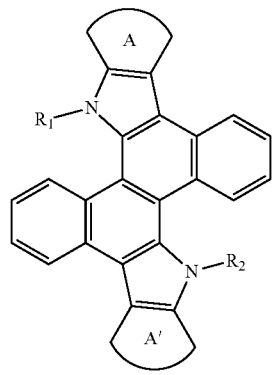

Formula 1

2. Description of the Related Art

Light-emitting devices are self-emitting display devices and have a wide viewing angle, a high contrast ratio, and a short response time. Due to these characteristics, light-emitting devices are drawing more attention.

Such organic light-emitting devices can be roughly classified as either inorganic light-emitting devices that include emission layers containing inorganic compounds, or organic light-emitting devices that include emission layers containing organic compounds.

Specifically, organic light-emitting devices have higher luminance, lower driving voltages, and shorter response times than inorganic light-emitting devices, and can render multi-colored displays. In addition, organic light-emitting devices produce various colors. Thus, much research into such organic light-emitting devices has been conducted.

Typically, an organic light-emitting device has a stack structure including an anode, a cathode, and an organic emission layer between the anode and the cathode. However, a hole injection layer, a hole transport layer, an electron transport layer, and/or an electron injection layer may be further stacked between the anode and the organic emission layer, or between the organic emission layer and the cathode. In other words, an organic light-emitting device may have either an anode/hole transport layer/organic emission layer/cathode structure or an anode/hole transport layer/organic emission layer/electron transport layer/cathode structure.

As a material for forming the organic emission layer, naphthalene derivatives may be used. However, organic light-emitting devices including such materials may not have satisfactory life span, efficiency, and power consumption characteristics. As such, improvements to the life span, efficiency, and/or power consumption characteristics are still desired.

SUMMARY

An aspect of an embodiment of the present invention is directed toward a heterocyclic compound having improved electrical characteristics, charge transporting capabilities, light-emission capabilities, and a high glass-transition temperature that is high enough to prevent or protect from crystallization.

An aspect of an embodiment of the present invention is directed toward an organic light-emitting device including the heterocyclic compound.

An aspect of an embodiment of the present invention is directed toward a flat panel display device including the organic light-emitting device.

According to an embodiment of the present invention, there is provided a heterocyclic compound represented by Formula 1 below:

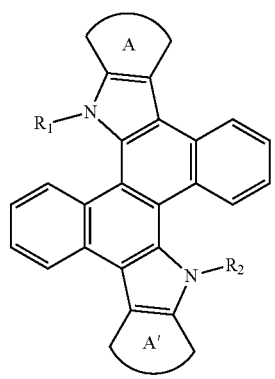

Formula 1 wherein in Formula 1, $R_1$ and $R_2$ are each independently selected from the group consisting of a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a substituted or unsubstituted $C_5$-$C_{60}$ aryloxy group, a substituted or unsubstituted $C_5$-$C_{60}$ arylthio group, a substituted or unsubstituted $C_5$-$C_{60}$ aryl group, a substituted amino group with a $C_5$-$C_{60}$ aryl or $C_3$-$C_{60}$ heteroaryl group, a substituted or unsubstituted $C_3$-$C_{60}$ heteroaryl group, a substituted or unsubstituted $C_6$-$C_{60}$ condensed polycyclic group, a halogen atom, a cyano group, a nitro group, a hydroxyl group, and a carboxyl group; and A and A' are each a substituted or unsubstituted pyridine ring.

In some embodiments, $R_1$ and $R_2$ in Formula 1 may be each independently selected from the group consisting of a hydrogen atom, a deuterium atom, a halogen atom, a cyano group, a $C_1$-$C_{40}$ alkyl group, and groups represented by Formulae 2a to 2h below:

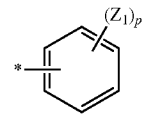

formula 2a

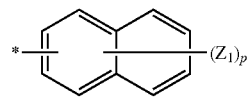

formula 2b formula 2c
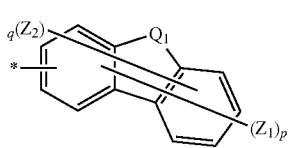

formula 2d
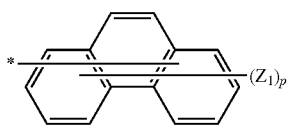

formula 2e
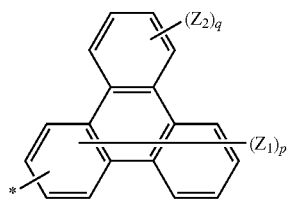

formula 2f
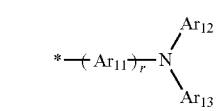

formula 2g
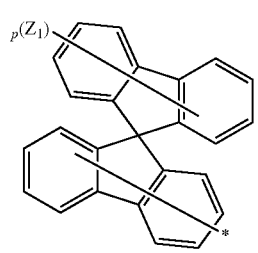

formula 2h
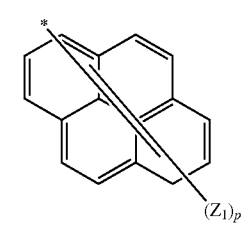

formula 3a
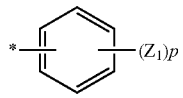

formula 3b
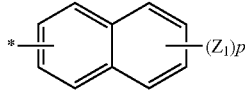

formula 3c
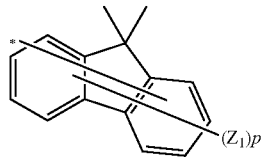

formula 3d
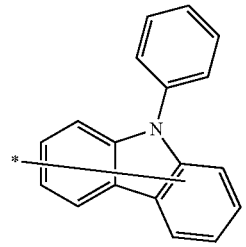

formula 3e

formula 3f
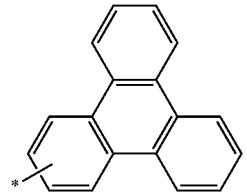

formula 3g
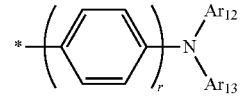

formula 3h
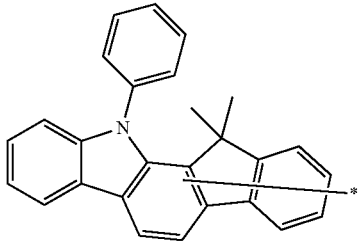

wherein, in Formulae 2a to 2h, $Q_1$ is a linking group represented by —$C(R_3)(R_4)$—, —$N(R_3)$—, —S—, or —O—; $Z_1$, $Z_2$, $Ar_{12}$, $Ar_{13}$, $R_3$, and $R_4$ are each independently selected from the group consisting of a hydrogen atom, a deuterium atom, a $C_1$-$C_{20}$ alkyl group, a substituted or unsubstituted $C_5$-$C_{20}$ aryl group, a substituted or unsubstituted $C_2$-$C_{20}$ heterocyclic group, an amino group substituted with a $C_5$-$C_{20}$ aryl group or $C_3$-$C_{20}$ heteroaryl group, a cyano group, a nitro group, a hydroxyl group, and a carboxy group, wherein adjacent $Z_1$ and/or $Z_2$ is linked to form a ring; $Ar_{11}$ is a substituted or unsubstituted $C_1$-$C_{20}$ alkylene group, a substituted or unsubstituted $C_5$-$C_{20}$ arylene group, or a substituted or unsubstituted $C_2$-$C_{20}$ heterocyclic divalent group; p is an integer from 1 to 12; q is an integer from 1 to 12; r is an integer from 1 to 5; and * indicates a binding site.

In some embodiments, $R_1$ and $R_2$ in Formula 1 may be each independently selected from the group consisting of a hydrogen atom, a deuterium atom, a halogen atom, a cyano group, a methyl group, an ethyl group, a propyl group, a butyl group, a t-butyl, a pentyl group, and groups represented by Formulae 3a to 3j below:

formula 3i

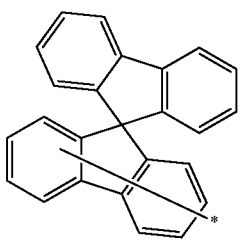

formula 3j

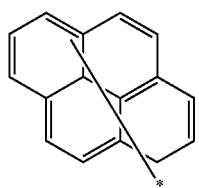

wherein, in Formulae 3a to 3j, $Z_1$, $Ar_{12}$, and $Ar_{13}$ are each independently selected from the group consisting of a hydrogen atom, a deuterium atom, an unsubstituted $C_5$-$C_{20}$ aryl group, and a substituted or unsubstituted $C_2$-$C_{20}$ heterocyclic group; r is an integer from 1 to 2; p is an integer from 1 to 5; and * indicates a binding site.

In some embodiments, the heterocyclic compound may include one of the compounds represented by Formulae 2 to 4:

formula 2

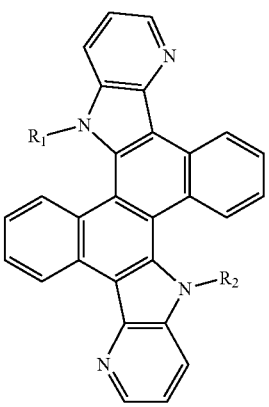

formula 3

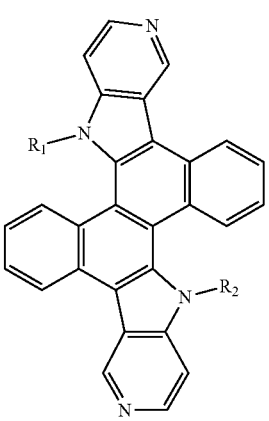

formula 4

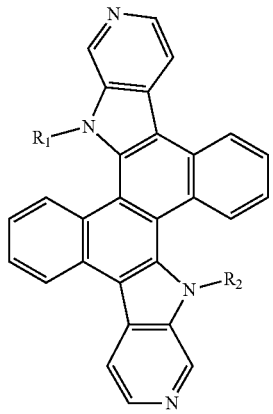

wherein, in Formulae 2 to 4, $R_1$ and $R_2$ are each independently selected from the group consisting of a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a substituted or unsubstituted $C_5$-$C_{60}$ aryloxy group, a substituted or unsubstituted $C_5$-$C_{60}$ arylthio group, a substituted or unsubstituted $C_5$-$C_{60}$ aryl group, a substituted amino group with a $C_5$-$C_{60}$ aryl or $C_3$-$C_{60}$ heteroaryl group, a substituted or unsubstituted $C_3$-$C_{50}$ heteroaryl group, a substituted or unsubstituted $C_6$-$C_{60}$ condensed polycyclic group, a halogen atom, a cyano group, a nitro group, a hydroxyl group, and a carboxyl group.

In some embodiments, $R_1$ and $R_2$ may be the same.

In some embodiments, A and A' may be the same.

In some embodiments, A and A' in Formula 1 may be the same, and $R_1$ and $R_2$ may be each independently selected from the group consisting of a hydrogen atom, a deuterium atom, a halogen atom, a cyano group, a methyl group, an ethyl group, a propyl group, a butyl group, a t-butyl, a pentyl group, and groups represented by Formulae 3a to 3j below:

formula 3a

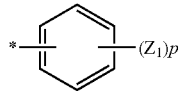

formula 3b

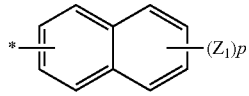

formula 3c

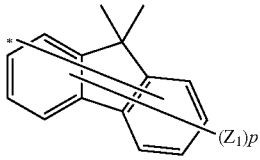

formula 3d

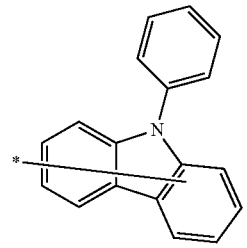

wherein, in Formulae 3a to 3j, $Z_1$, $Ar_{12}$, and $Ar_{13}$ are each independently selected from the group consisting of a hydrogen atom, a deuterium atom, an unsubstituted $C_5$-$C_{20}$ aryl group, and a substituted or unsubstituted $C_2$-$C_{20}$ heterocyclic group; r is an integer from 1 to 2; p is an integer from 1 to 5; and * indicates a binding site.

In some embodiments, $R_1$ and $R_2$ in Formula 1 may be the same, and may be selected from the group consisting of a hydrogen atom, a deuterium atom, a halogen atom, a cyano group, a methyl group, an ethyl group, a propyl group, a butyl group, a t-butyl, a pentyl group, and groups represented by Formulae 3a to 3j below:

formula 3i

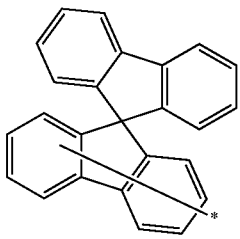

formula 3j

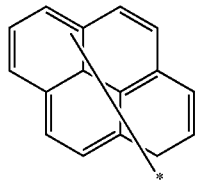

wherein, in Formulae 3a to 3j, $Z_1$, $Ar_{12}$, and $Ar_{13}$ are each independently selected from the group consisting of a hydrogen atom, a deuterium atom, an unsubstituted $C_5$-$C_{20}$ aryl group, and a substituted or unsubstituted $C_2$-$C_{20}$ heterocyclic group; r is an integer from 1 to 2; p is an integer from 1 to 5; and * indicates a binding site.

In some embodiments, the heterocyclic compound may include one of the compounds represented by Formulae 2 to 4:

formula 2

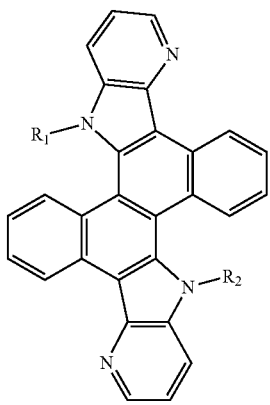

formula 3

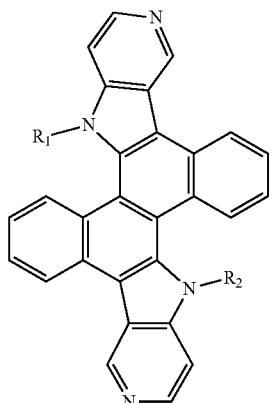

formula 4

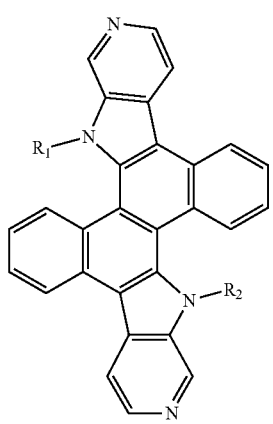

wherein, in Formulae 2 to 4, $R_1$ and $R_2$ are the same, and are selected from among a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a substituted or unsubstituted $C_5$-$C_{60}$ aryloxy group, a substituted or unsubstituted $C_5$-$C_{60}$ arylthio group, a substituted or unsubstituted $C_5$-$C_{60}$ aryl group, a substituted amino group with a $C_5$-$C_{60}$ aryl or $C_3$-$C_{60}$ heteroaryl group, a substituted or unsubstituted $C_3$-$C_{60}$ heteroaryl group, a substituted or unsubstituted $C_6$-$C_{60}$ condensed polycyclic group, a halogen atom, a cyano group, a nitro group, a hydroxyl group, and a carboxyl group.

In some embodiments, the heterocyclic compound may include one of the compounds below:

3

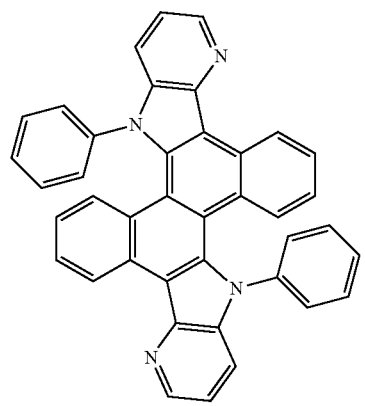

5

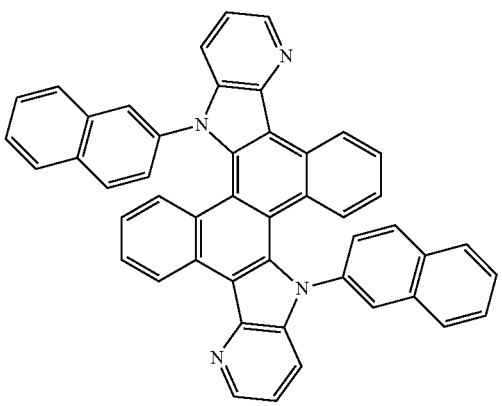

-continued
11
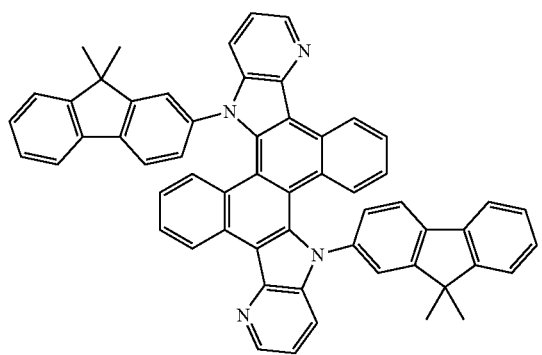
18
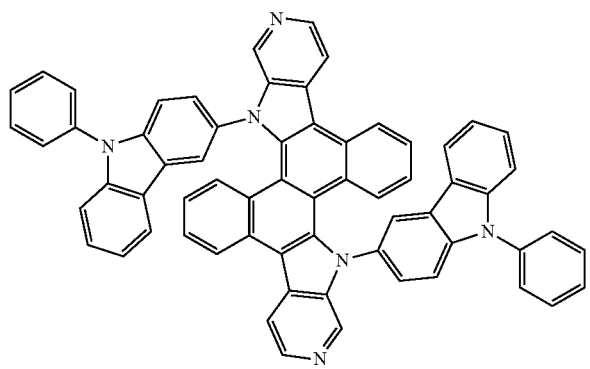
23
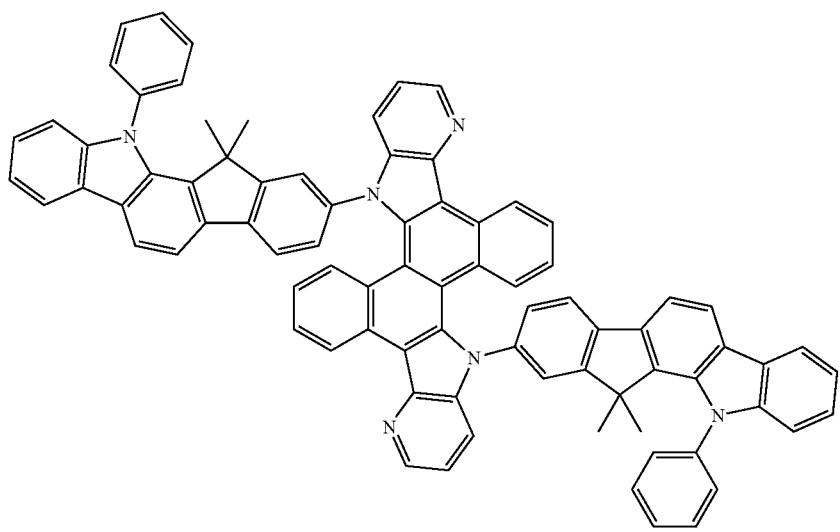
39
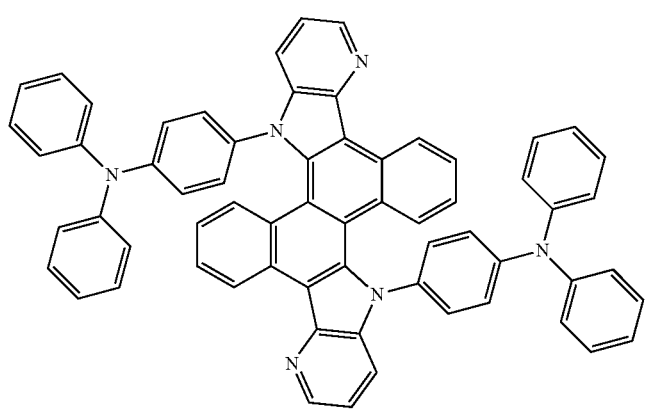

-continued

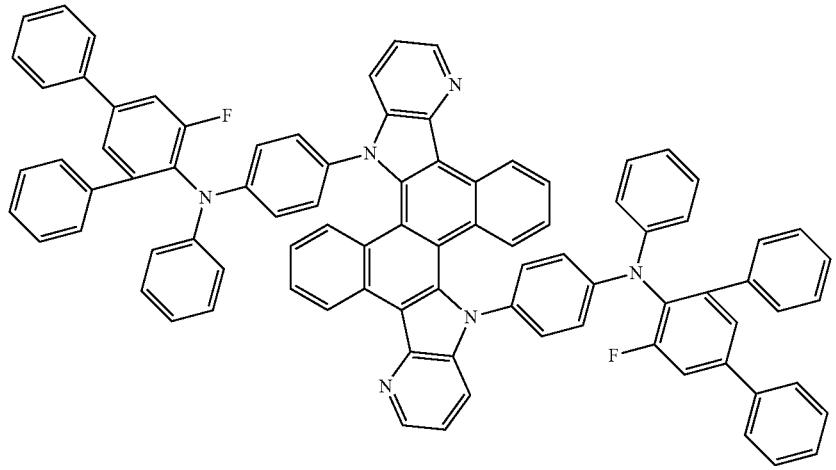

According to another embodiment of the present invention, there is provided an organic light-emitting device including: a first electrode; a second electrode; and an organic layer disposed between the first electrode and the second electrode, the organic layer including a first layer including the above-described heterocyclic compound.

In some embodiments, the organic layer may include a hole injection layer, a hole transport layer, a functional layer having both hole injection and hole transport capabilities, an electron injection layer, an electron transport layer, or a functional layer having both electron injection and electron transport capabilities.

In some embodiments, the first layer may include an emission layer, and the heterocyclic compound may be used as a host or dopant for a fluorescent or phosphorescent device.

In some embodiments, the organic layer may include an emission layer, a hole transport layer, and an electron transport layer, either one of which may include the heterocyclic compound, and the emission layer may further include an anthracene compound, an arylamine compound, or a styryl compound.

In some embodiments the organic layer may include an emission layer, a hole transport layer, and an electron transport layer, either one of which may include the heterocyclic compound, and either red, green, blue, or white layer of the emission layer may include a phosphorescent compound.

In some embodiments the organic light-emitting device may include a plurality of organic layers, at least one of which is formed using the heterocyclic compound by a wet process.

According to another embodiment of the present invention, a flat panel display device includes the above-described organic light-emitting device, wherein the first electrode of the organic light-emitting device is electrically connected to a source electrode or a drain electrode of a thin-film transistor.

BRIEF DESCRIPTION OF THE DRAWING

The above and other features and advantages of the present invention will become more apparent by describing in detail exemplary embodiments thereof with reference to the attached drawing, which illustrates the structure of an organic light-emitting device according to an embodiment of the present invention.

DETAILED DESCRIPTION

An organic light-emitting device manufactured using a compound of phenylanthracene dimer or trimer as an organic emission layer material is known. However, such organic light-emitting devices have a narrow energy gap and lower blue-light color purity since two or three oligomeric species of anthracene are linked by conjugation. In addition, such compounds are highly vulnerable to oxidation and thus are liable to produce impurities, thereby necessitating purification. In order to overcome these drawbacks, organic light-emitting devices (that are manufactured using an anthracene compound including naphthalene substituted for anthracene at the 1,9 positions, or using a diphenylanthracene compound including an aryl group substituted for a phenyl group at the m-position) have been introduced. However, these organic light-emitting devices have a lower light-emission efficiency.

Organic light-emitting devices may be manufactured using nathphalene-substituted monoanthracene derivatives. However, the light-emission efficiency thereof is low (e.g., at about 1 cd/A), and thus such organic light-emitting devices are not suitable for practical use.

Furthermore, organic light-emitting devices may be manufactured using phenylanthracene compounds including aryl substituents at the m-position. Such a compound has high thermal resistance, but leads to an unsatisfactorily low light-emission efficiency of about 2 cd/A.

Embodiments of the present invention will now be described more fully with reference to the accompanying drawings, in which certain exemplary embodiments of the invention are shown.

An aspect of the present invention provides a heterocyclic compound represented by Formula 1 below.

Formula 1

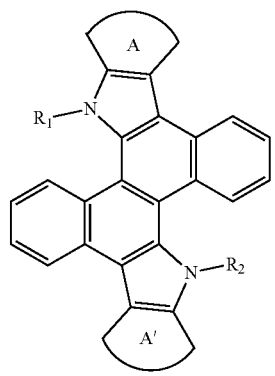

In Formula 1, $R_1$ and $R_2$ are each independently a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_{30}$-$C_{60}$ cycloalkyl group, a substituted or unsubstituted $C_1$-$C_{60}$ alkoxy group, a substituted or unsubstituted $C_5$-$C_{60}$ aryloxy group, a substituted or unsubstituted $C_5$-$C_{60}$ arylthio group, a substituted or unsubstituted $C_5$-$C_{60}$ aryl group, a substituted amino group with a $C_5$-$C_{60}$ aryl or $C_3$-$C_{60}$ heteroaryl group, a substituted or unsubstituted $C_3$-$C_{60}$ heteroaryl group, a substituted or unsubstituted $C_6$-$C_{60}$ condensed polycyclic group, a halogen atom, a cyano group, a nitro group, a hydroxyl group, or a carboxyl group; and A and A' are each a substituted or unsubstituted pyridine ring.

In some embodiments the heterocyclic compound of Formula 1 may be used as a light-emitting material, an electron-transporting material or an electron-injecting material for organic light-emitting devices. The heterocyclic compound of Formula 1 having a heterocyclic group in the molecules thereof has a high glass transition temperature (Tg) or a high melting point due to the inclusion of the heterocyclic group. Thus, the heterocyclic compound has high heat resistance against Joule's heat generated in an organic layer, between organic layers, or between an organic layer and a metal electrode when light emission occurs, and has high durability in high-temperature environments.

An organic light-emitting device manufactured using the compound of Formula 1 has high durability when stored or operated. In addition, due to the inclusion of a substituent such as an aryl group or heteroaryl group, molecular layers formed as thin films may be maintained in good condition, thereby improving the characteristics of the organic light-emitting device.

Substituents in the heterocyclic compound of Formula 1 will now be described in more detail.

In some embodiments, $R_1$ and $R_2$ in Formula 1 may be each independently a hydrogen atom, a deuterium atom, a halogen atom, a cyano group, a $C_1$-$C_{40}$ alkyl group, or groups represented by Formulae 2a to 2h below:

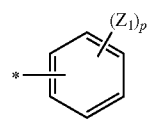

formula 2a

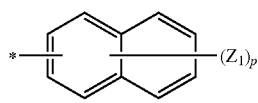

formula 2b

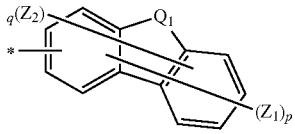

formula 2c

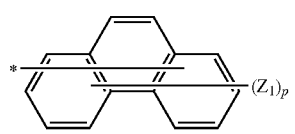

formula 2d

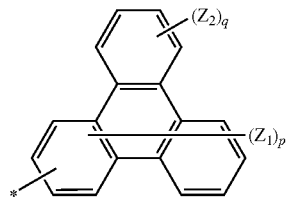

formula 2e

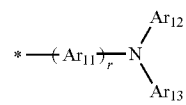

formula 2f

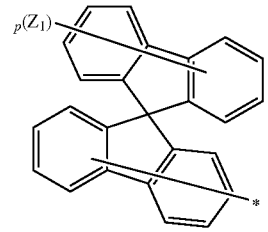

formula 2g

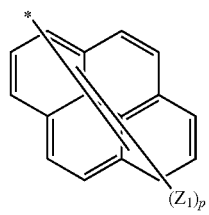

formula 2h

In Formulae 2a to 2h, $Q_1$ is a linking group represented by —$C(R_3)(R_4)$—, —$N(R_3)$—, —S—, or —O—;

$Z_1$, $Z_2$, $Ar_{12}$, $Ar_{13}$, $R_3$, and $R_4$ are each independently a hydrogen atom, a deuterium atom, a $C_1$-$C_{20}$ alkyl group, a substituted or unsubstituted $C_5$-$C_{20}$ aryl group, a substituted or unsubstituted $C_2$-$C_{20}$ heterocyclic group, an amino group substituted with a $C_5$-$C_{20}$ aryl group or $C_3$-$C_{20}$ heteroaryl group, a cyano group, a nitro group, a hydroxyl group, or a carboxy group, wherein adjacent $Z_1$ and/or $Z_2$ is linked to form a ring; $Ar_{11}$ is a substituted or unsubstituted $C_1$-$C_{20}$ alkylene group, a substituted or unsubstituted $C_5$-$C_{20}$ arylene group, or a substituted or unsubstituted $C_2$-$C_{20}$ heterocyclic divalent group; and p is an integer from 1 to 12; q is an integer from 1 to 12; r is an integer from 1 to 5; and * indicates a binding site.

In some embodiments, $R_1$ and $R_2$ in Formula 1 above may be each independently a hydrogen atom, a deuterium atom, a halogen atom, a cyano group, a methyl group, an ethyl group, a propyl group, a butyl group, a t-butyl, a pentyl group, or groups represented by Formulae 3a to 3j below:

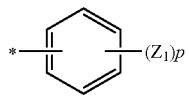

formula 3a

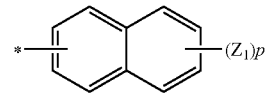

formula 3b

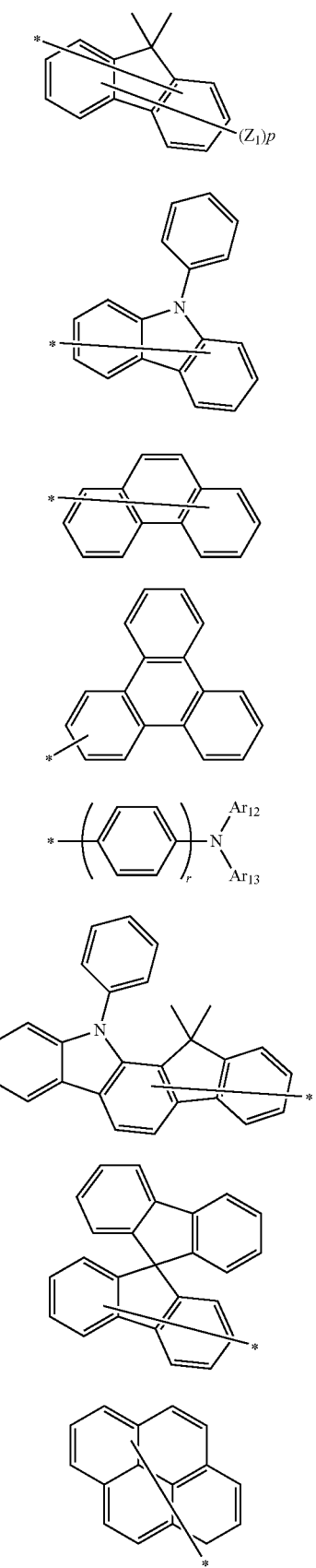

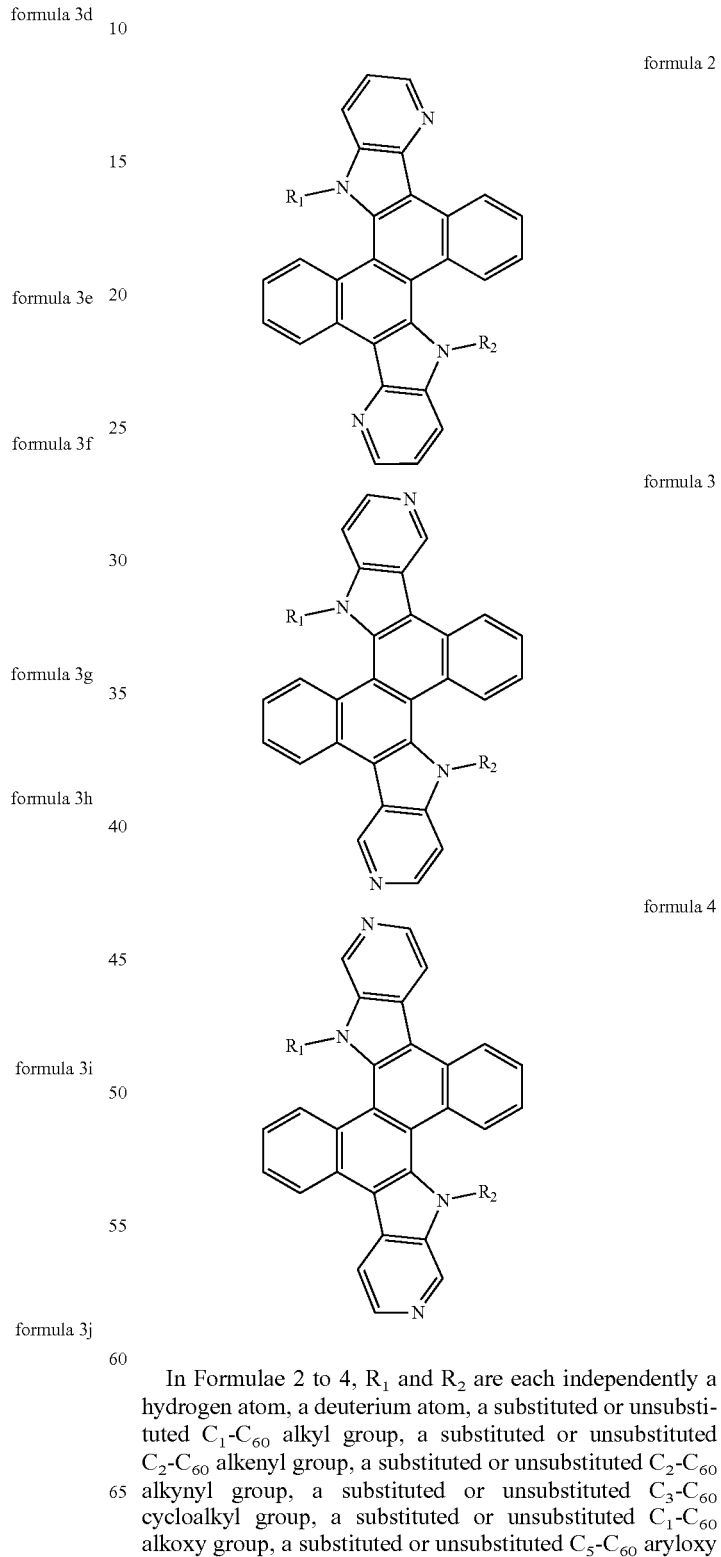

In Formulae 3a to 3h above, $Z_1$, $Ar_{12}$, and $Ar_{13}$ are each independently a hydrogen atom, a deuterium atom, an unsubstituted $C_5$-$C_{20}$ aryl group, or a substituted or unsubstituted $C_2$-$C_{20}$ heterocyclic group; r is an integer from 1 to 2; p is an integer from 1 to 5; and * indicates a binding site.

In some embodiments, the heterocyclic compound of Formula 1 above may be a compound represented by any of Formulae 2 to 4 below.

In Formulae 2 to 4, $R_1$ and $R_2$ are each independently a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a substituted or unsubstituted $C_5$-$C_{60}$ aryloxy group, a substituted or unsubstituted $C_5$-$C_{60}$ arylthio group, a substituted or unsubstituted $C_5$-$C_{60}$ aryl group, a substituted amino group with a $C_5$-$C_{60}$ aryl or $C_3$-$C_{60}$ heteroaryl group, a substituted or unsubstituted $C_3$-$C_{60}$ heteroaryl group, a substituted or unsubstituted $C_6$-$C_{60}$ condensed polycyclic group, a halogen atom, a cyano group, a nitro group, a hydroxyl group, or a carboxyl group;

In some embodiments, $R_1$ and $R_2$, or A and A' may be the same.

In some embodiments, A and A' in Formula 1 above may be the same, and $R_1$ and $R_2$ may be each independently a hydrogen atom, a deuterium atom, a halogen atom, a cyano group, a methyl group, an ethyl group, a propyl group, a butyl group, a t-butyl, a pentyl group, or groups represented by Formulae 3a to 3j below:

formula 3a formula 3b formula 3c formula 3d formula 3e formula 3f formula 3g

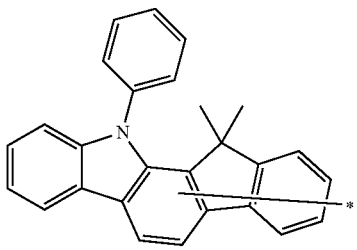
formula 3h

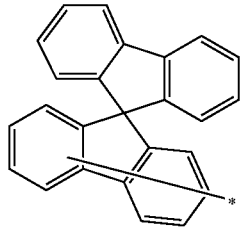
formula 3i

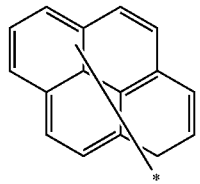
formula 3j

In Formulae 3a to 3j above, $Z_1$, $Ar_{12}$, and $Ar_{13}$ are each independently a hydrogen atom, a deuterium atom, an unsubstituted $C_5$-$C_{20}$ aryl group, or a substituted or unsubstituted $C_2$-$C_{20}$ heterocyclic group; r is an integer from 1 to 2; p is an integer from 1 to 5; and * indicates a binding site.

In some embodiments $R_1$ and $R_2$ in Formula 1 above may be the same, and may be selected from among a hydrogen atom, a deuterium atom, a halogen atom, a cyano group, a methyl group, an ethyl group, a propyl group, a butyl group, a t-butyl, a pentyl group, and groups represented by Formulae 3a to 3j below:

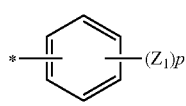
formula 3a

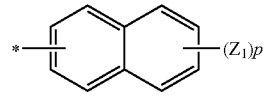
formula 3b

formula 3c

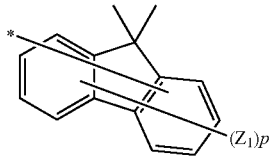
formula 3d

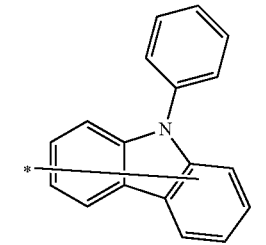

-continued formula 3e
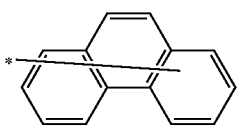

formula 3f
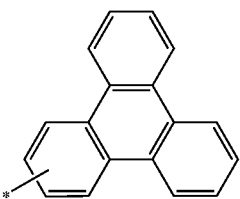

formula 3g
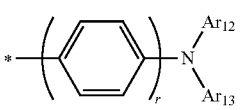

formula 3h
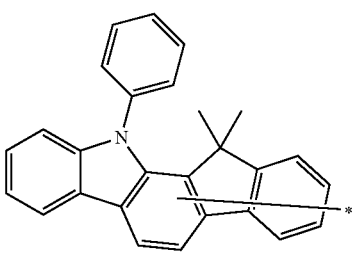

formula 3i
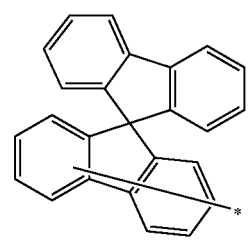

formula 3j
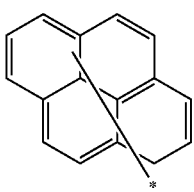

In Formulae 3a to 3j above, $Z_1$, $Ar_{12}$, and $Ar_{13}$ are each independently a hydrogen atom, a deuterium atom, an unsubstituted $C_5$-$C_{20}$ aryl group, or a substituted or unsubstituted $C_2$-$C_{20}$ heterocyclic group; r is an integer from 1 to 2; p is an integer from 1 to 5; and * indicates a binding site.

In some embodiments the heterocyclic compound of Formula 1 above may be a compound represented by any of Formulae 2 to 4 below.

formula 2 formula 3 formula 4

In Formulae 2 to 4, $R_1$ and $R_2$ are the same, and are selected from among a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a substituted or unsubstituted $C_5$-$C_{60}$ aryloxy group, a substituted or unsubstituted $C_5$-$C_{60}$ arylthio group, a substituted or unsubstituted $C_5$-$C_{60}$ aryl group, a substituted amino group with a $C_5$-$C_{60}$ aryl or $C_2$-$C_{20}$ heteroaryl group, a substituted or unsubstituted $C_3$-$C_{60}$ heteroaryl group, a substituted or unsubstituted $C_6$-$C_{60}$ condensed polycyclic group, a halogen atom, a cyano group, a nitro group, a hydroxyl group, and a carboxyl group.

Hereinafter, substituents described with reference to the formulae will now be described in more detail. In this regard, the numbers of carbons in substituents are presented only for illustrative purposes and do not limit the characteristics of the substituents.

The unsubstituted $C_1$-$C_{60}$ alkyl group used herein may be linear or branched. Examples of the alkyl group may include, but are not limited to, a methyl group, an ethyl group, a propyl group, an isobutyl group, a sec-butyl group, a pentyl group, an iso-amyl group, a hexyl group, a heptyl group, an octyl group, a nonanyl group, and a dodecyl group. At least one hydrogen atom of the alkyl group may be substituted with heavy hydrogen atom, a halogen atom, a hydroxyl group, a nitro group, a cyano group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, or a $C_3$-$C_{16}$ heteroaryl group.

The unsubstituted $C_2$-$C_{60}$ alkenyl group indicates an unsaturated alkyl group having at least one carbon-carbon double bond in the chain of the alkyl group. Examples of the alkenyl group include an ethenyl group, a propenyl group, a butenyl group, and the like. At least one hydrogen atom in the unsubstituted alkenyl group may be substituted with a substituent described above in conjunction with the alkyl group.

The unsubstituted $C_2$-$C_{60}$ alkynyl group indicates an alkyl group having at least one carbon-carbon triple bond in the chain of the alkyl group. Examples of the unsubstituted $C_2$-$C_{20}$ alkynyl group include acetylene, propylene, phenylacetylene, naphthylacetylene, isopropylacetylene, t-butylacetylene, diphenylacetylene, and the like. At least one hydrogen atom in the alkynyl group may be substituted with a substituent described above in conjunction with the alkyl group.

The unsubstituted $C_3$-$C_{50}$ cycloalkyl group used herein refers to a $C_3$-$C_{50}$ cyclic alkyl group wherein at least one hydrogen atom in the cycloalkyl group may be substituted with a substituent such as those described above in connection with the $C_1$-$C_{50}$ alkyl group.

The unsubstituted $C_1$-$C_{50}$ alkoxy group used herein is a group having a structure of —OA, wherein A is an unsubstituted $C_1$-$C_{50}$ alkyl group as described above. Examples of the unsubstituted $C_1$-$C_{50}$ alkoxy group include, but are not limited to, a methoxy group, an ethoxy group, a propoxy group, an isopropyloxy group, a butoxy group, and a pentoxy group. At least one hydrogen atom of the alkoxy group may be substituted with a substituent such as those described above in conjunction with the alkyl group.

The unsubstituted $C_5$-$C_{50}$ aryl group indicates a carbocyclic aromatic system containing at least one ring. At least two rings may be fused to each other or linked to each other by a single bond. The term 'aryl' refers to an aromatic system, such as phenyl, naphthyl, or anthracenyl. At least one hydrogen atom in the aryl group may be substituted with the substituents described with reference to the unsubstituted $C_1$-$C_{50}$ alkyl group.

Examples of the substituted or unsubstituted $C_5$-$C_{50}$ aryl group include, but are not limited to, a phenyl group, a $C_1$-$C_{10}$ alkylphenyl group (for example, ethylphenyl group), a halophenyl group (for example, o-, m-, and p-fluorophenyl group, dichlorophenyl group, etc.), a cyanophenyl group, dicyanophenyl group, a trifluoromethoxyphenyl group, a biphenyl group, a halobiphenyl group, a cyanobiphenyl group, a $C_1$-$C_{10}$ alkyl biphenyl group, a $C_1$-$C_{10}$ alkoxybiphenyl group, an o-, m-, and p-toryl group, an o-, m-, and p-cumenyl group, a mesityl group, a phenoxyphenyl group, a (α,α-dimethylbenzene)phenyl group, an (N,N'-dimethyl) aminophenyl group, an (N,N'-diphenyl)aminophenyl group, a pentalenyl group, an indenyl group, a naphthyl group, a halonaphthyl group (for example, fluoronaphthyl group), a $C_1$-$C_{10}$ alkylnaphthyl group (for example, methylnaphthyl group), a $C_1$-$C_{10}$ alkoxynaphthyl group (for example, methoxynaphthyl group), a cyanonaphthyl group, an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylene group, a pyrenyl group, a chrycenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronelyl group, a trinaphthylenyl group, a heptaphenyl group, a heptacenyl group, a pyranthrenyl group, and an ovalenyl group.

The unsubstituted $C_4$-$C_{60}$ heteroaryl group used herein includes one, two, or three hetero atoms selected from N, O, P, and S. At least two rings may be fused to each other or linked to each other by a single bond. Examples of the unsubstituted $C_4$-$C_{60}$ heteroaryl group include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazol group, an indol group, a quinolyl group, an isoquinolyl group, and a dibenzothiophene group. In addition, at least one hydrogen atom in the heteroaryl group may be substituted with a substituent described above in conjunction with the unsubstituted $C_1$-$C_{50}$ alkyl group.

The unsubstituted $C_5$-$C_{50}$ aryloxy group is a group represented by —OA$_1$ wherein A$_1$ may be a $C_5$-$C_{50}$ aryl group. An example of the aryloxy group is a phenoxy group. At least one hydrogen atom in the aryloxy group may be substituted with a substituent described above in conjunction with the unsubstituted $C_1$-$C_{50}$ alkyl group.

The unsubstituted $C_5$-$C_{50}$ arylthio group is a group represented by —SA$_1$ where A$_1$ may be a $C_5$-$C_{50}$ aryl group. Non-limiting examples of the arylthio group include a benzenethio group and a naphthylthio group. At least one hydrogen atom in the arylthio group may be substituted with a substituent described above in conjunction with the unsubstituted $C_1$-$C_{50}$ alkyl group.

The unsubstituted $C_6$-$C_{60}$ condensed polycyclic group used herein refers to a substituent including at least two rings wherein at least one aromatic ring and/or at least one non-aromatic ring are fused to each other. The unsubstituted $C_6$-$C_{60}$ condensed polycyclic group may include some of the substituents described in conjunction with the aryl group or the heteroaryl group.

Examples of the heterocyclic compound represented by Formula 1 include Compounds 1 through 42 represented by the following formulae. However, the compounds represented by Formula 1 are not limited thereto.

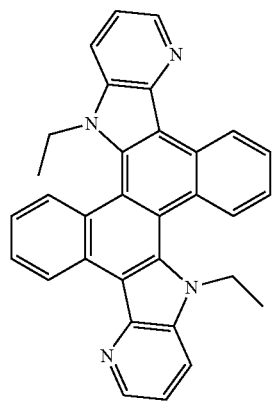
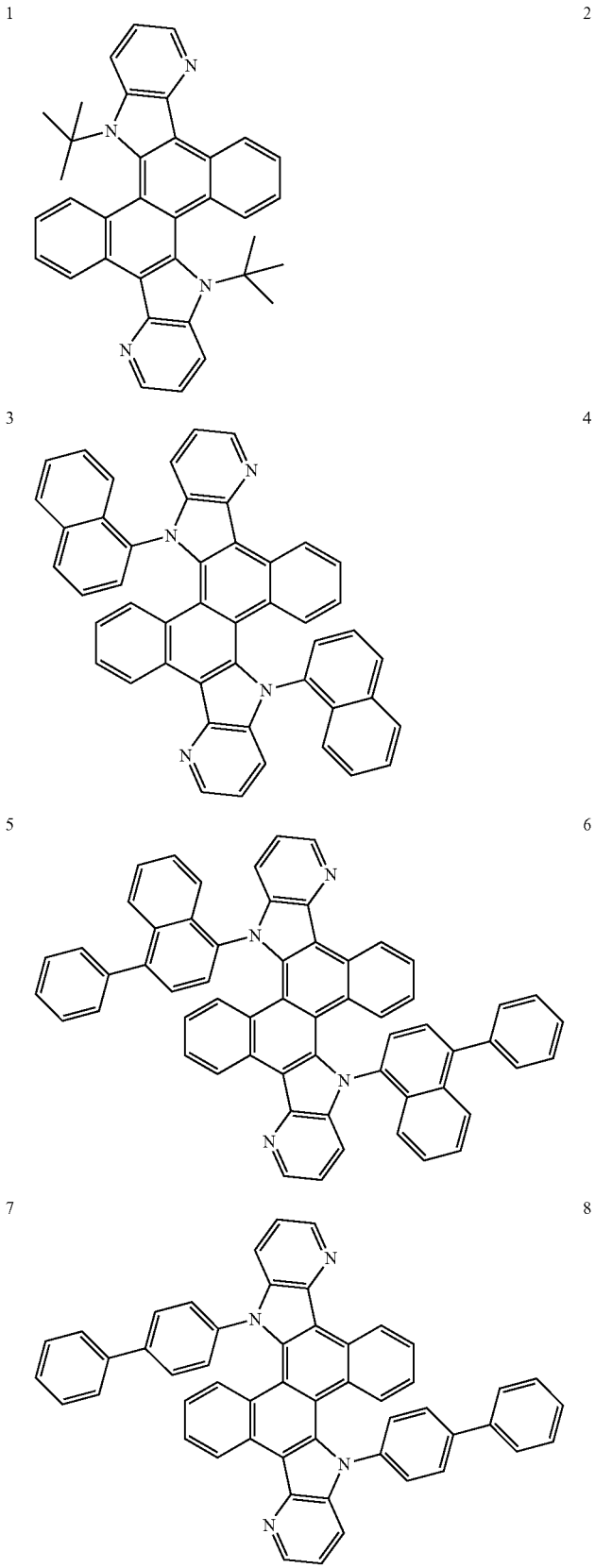

9
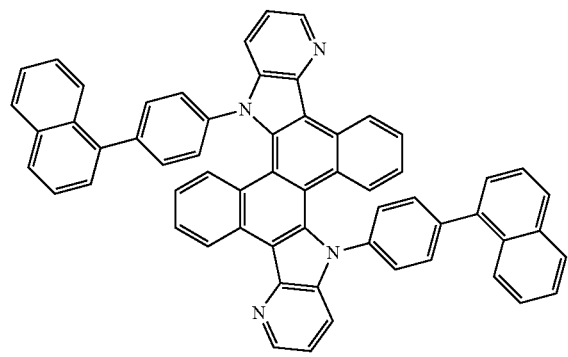
10
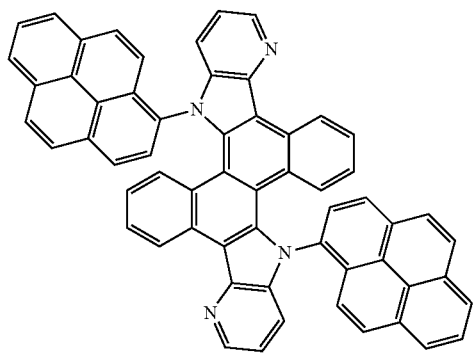
11
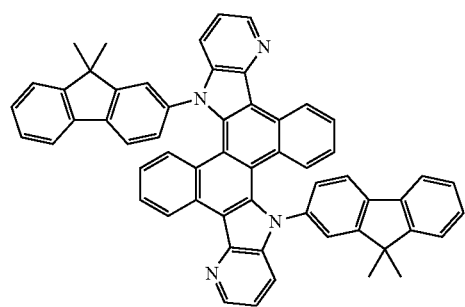
12
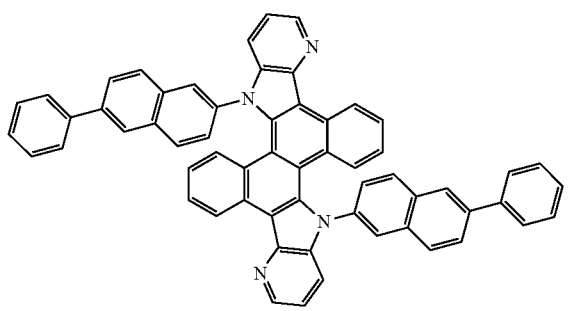
13
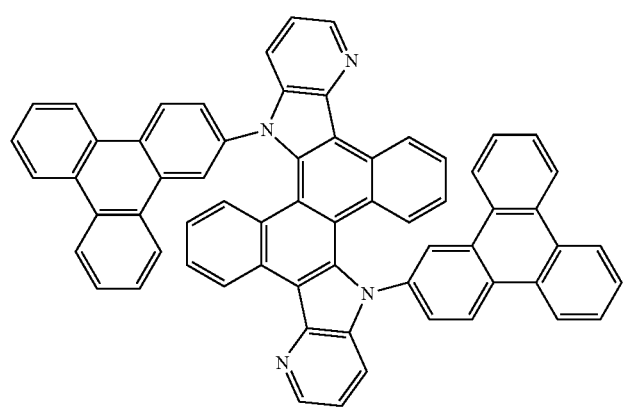
14
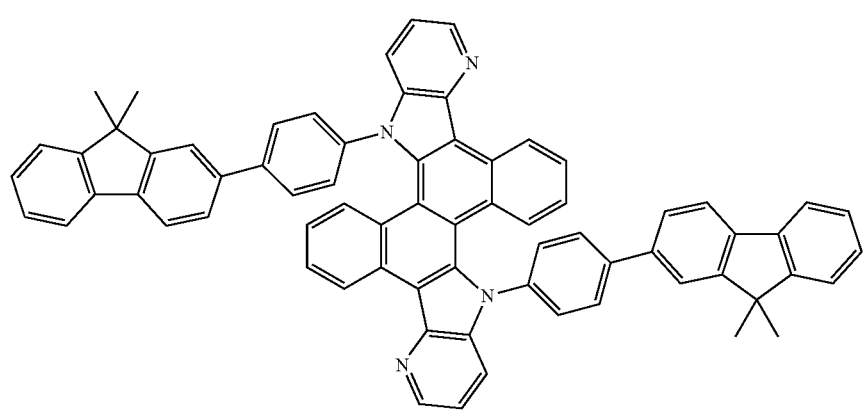

-continued
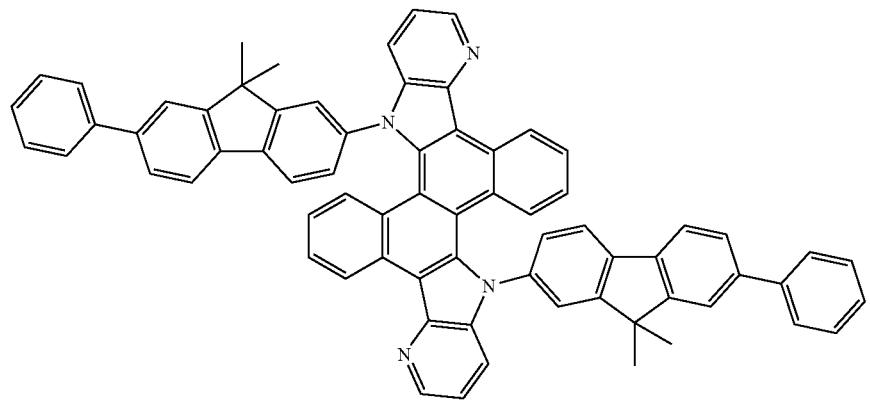
15
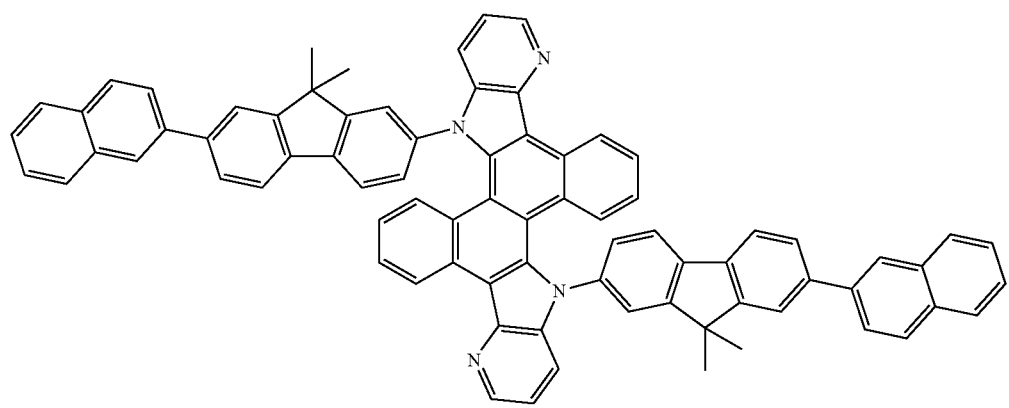
16
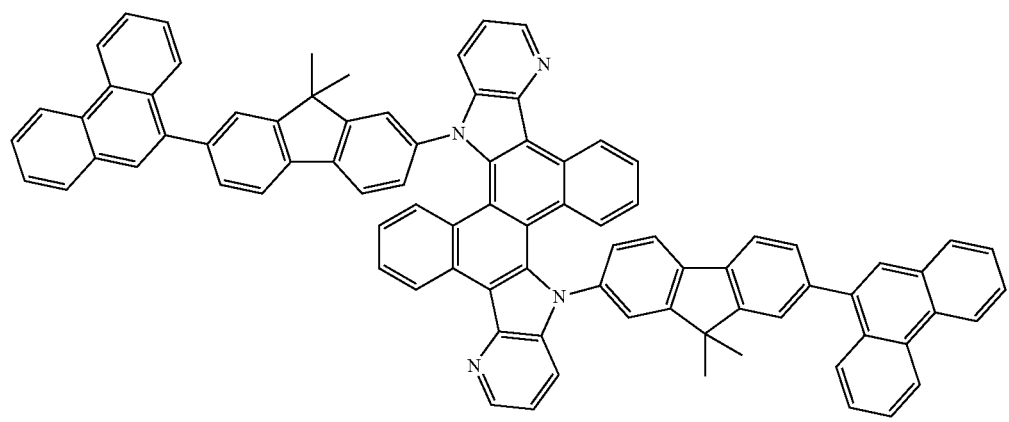
17
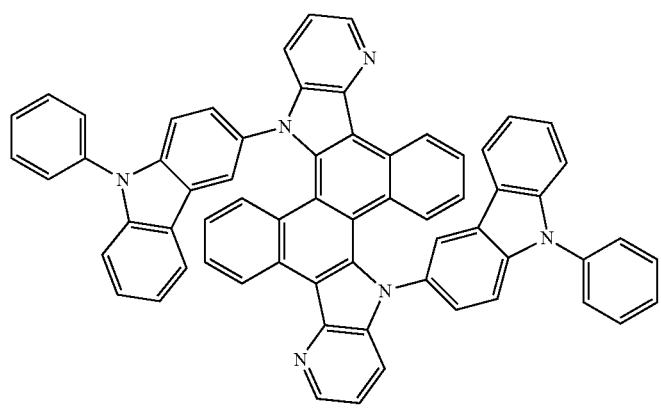
18

-continued
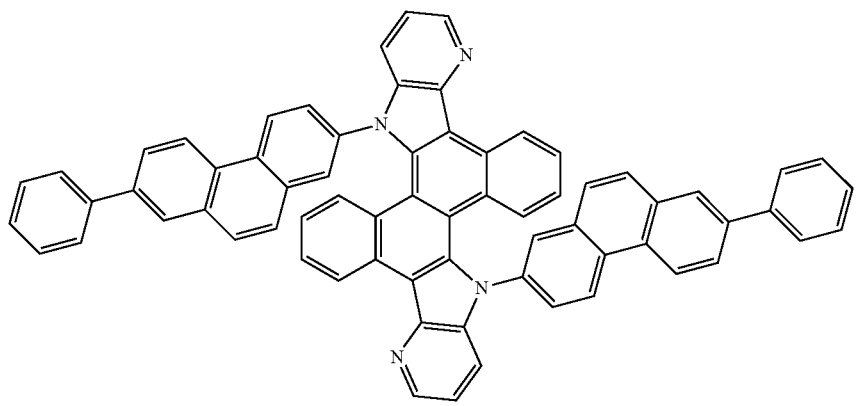
19
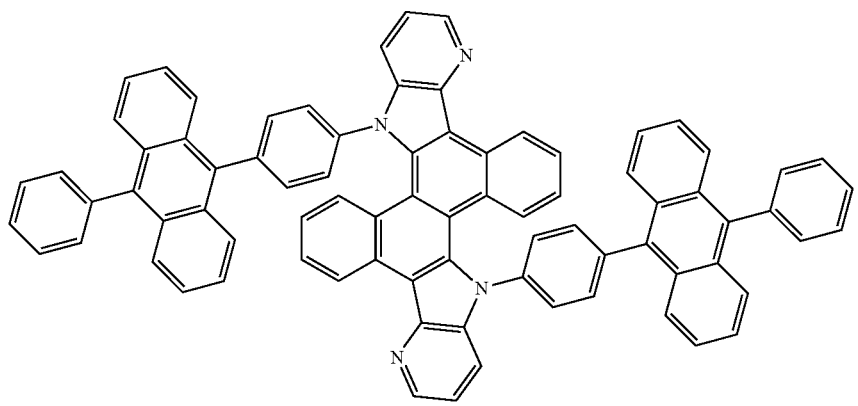
20
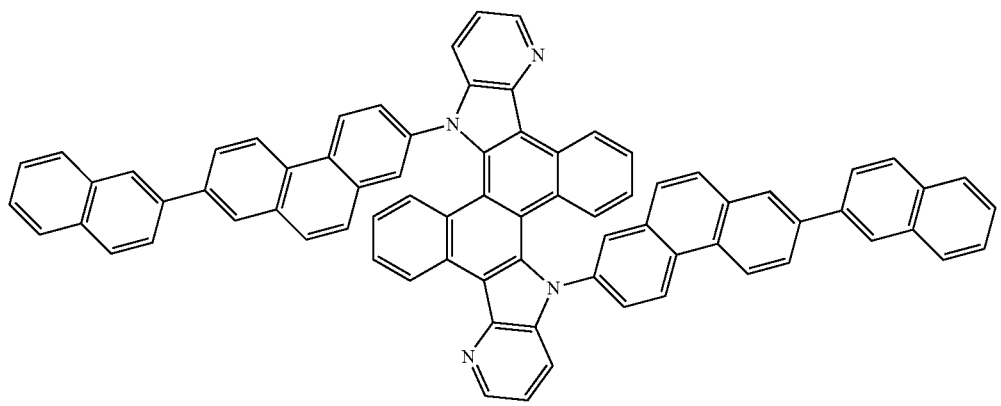
21
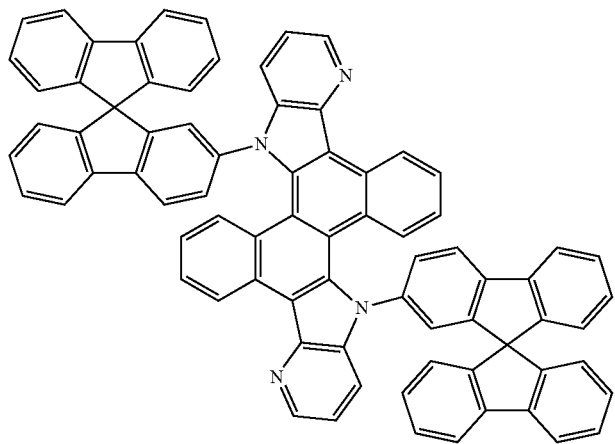
22

-continued
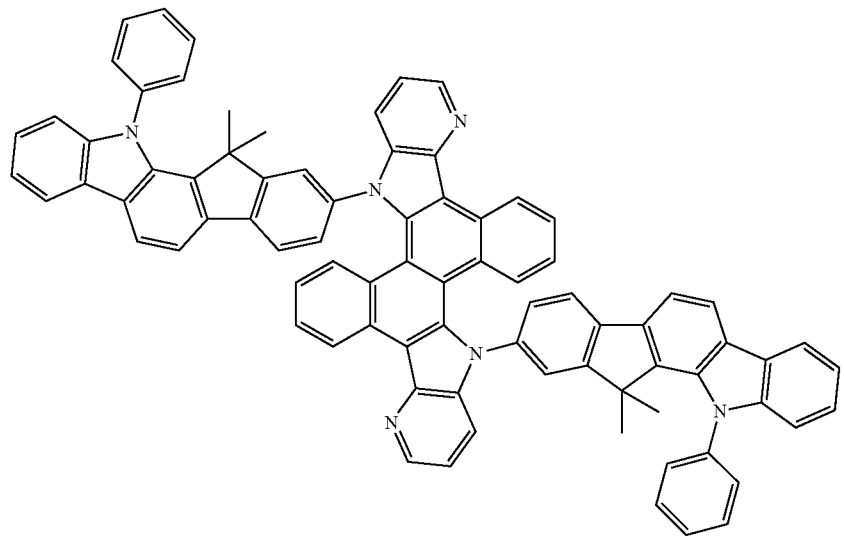
23
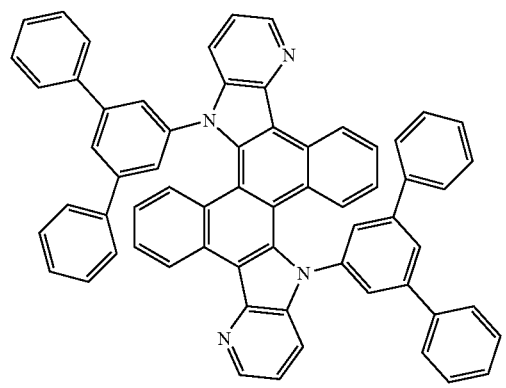
24
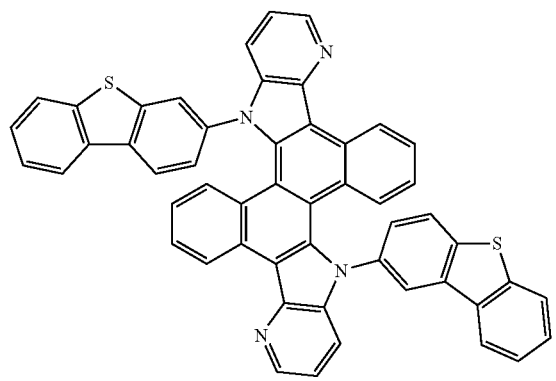
25
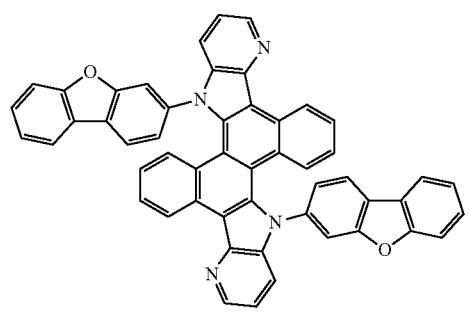
26
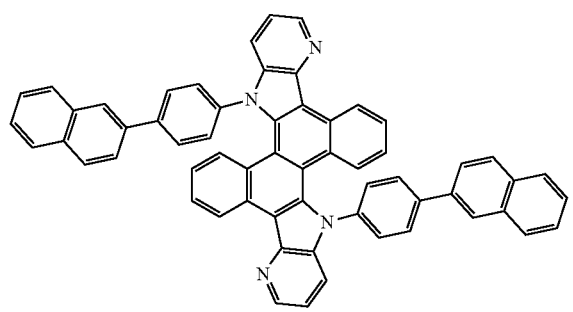
27
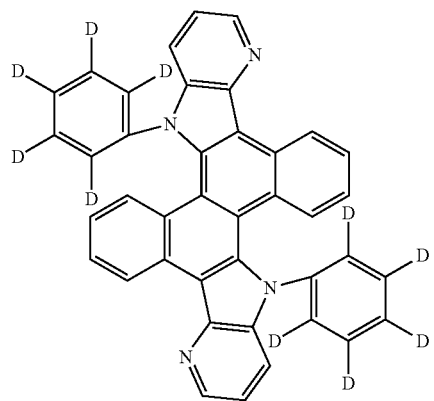
28
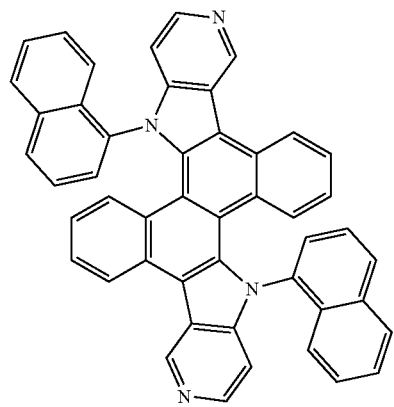
29

-continued
30
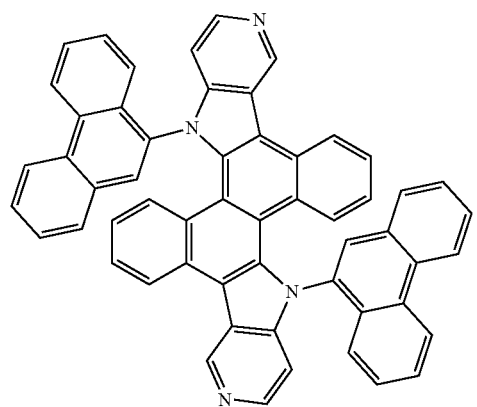
31
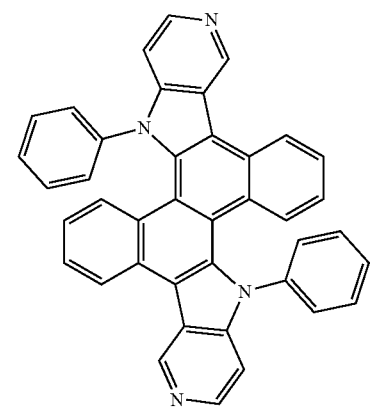
32
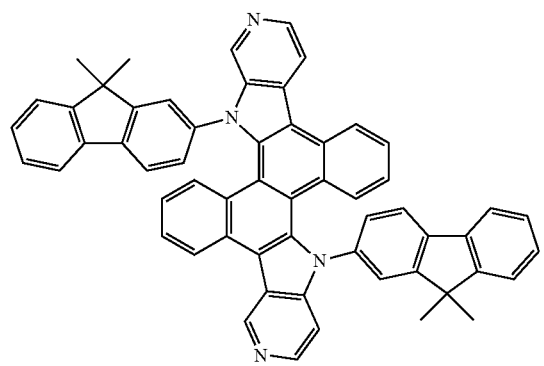
33
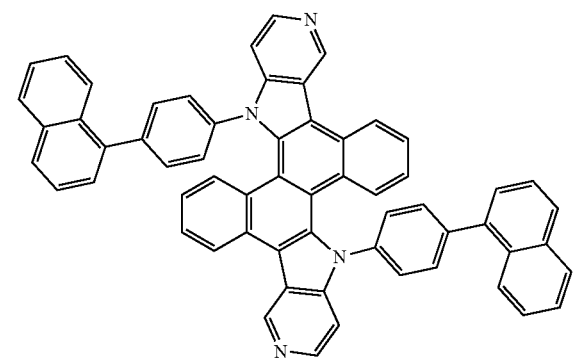
34
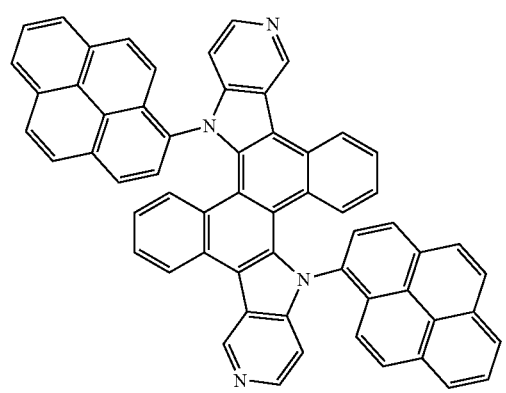
35
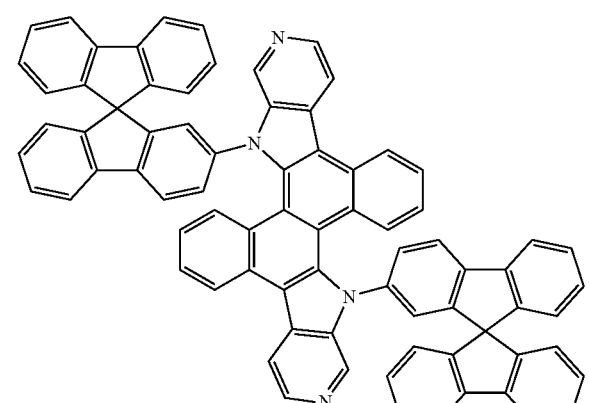
36
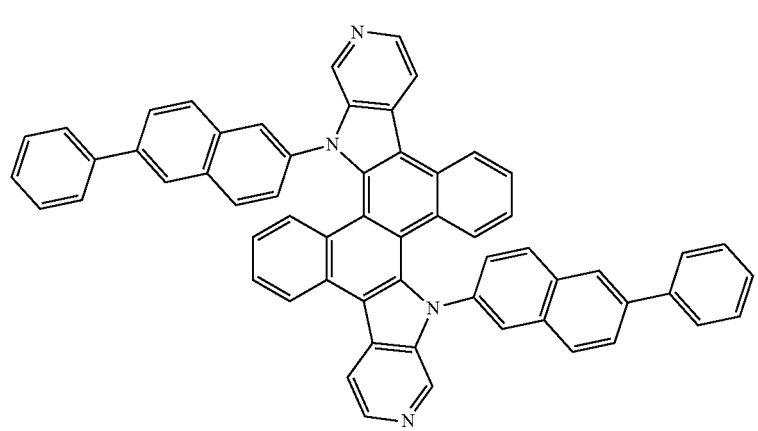

-continued
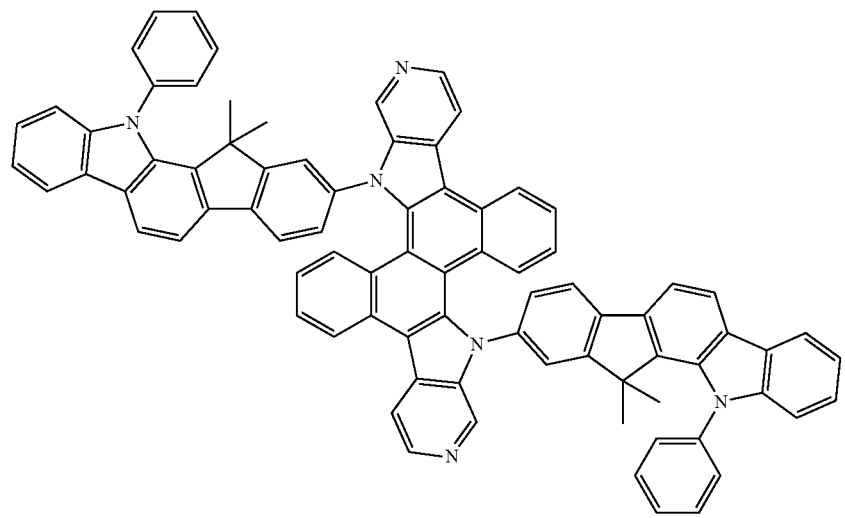
37
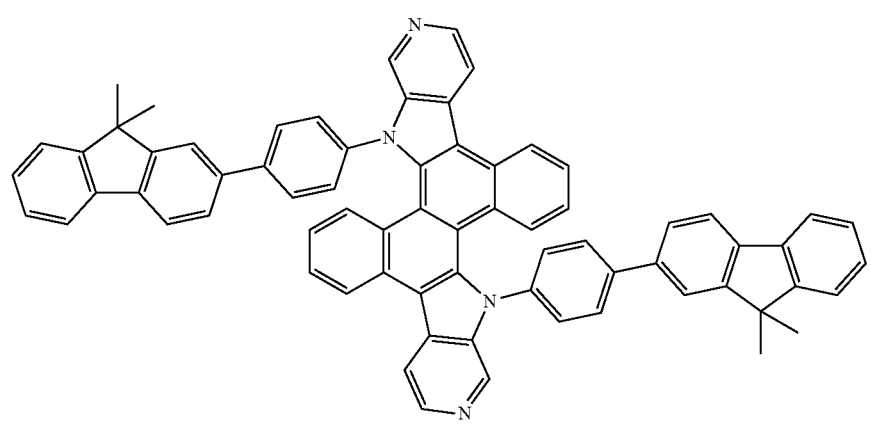
38
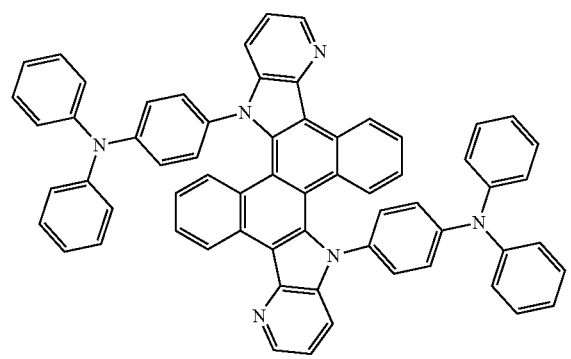
39
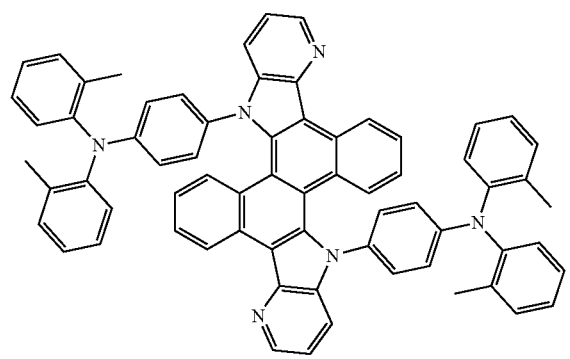
40

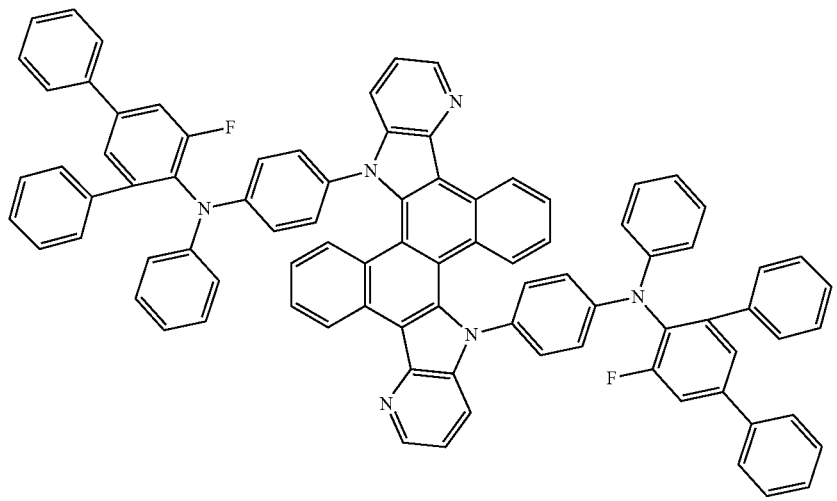

41

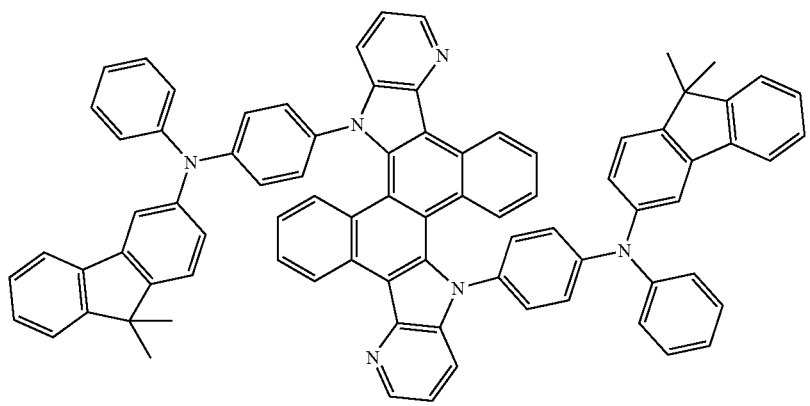

42

Another embodiment of the present invention provides an organic light-emitting device including a first electrode, a second electrode, and an organic layer disposed between the first electrode and the second electrode, wherein the organic layer may include a first layer containing the heterocyclic compound of Formula 1 described above.

The organic layer containing the heterocyclic compound may include a hole injection layer, a hole transport layer, a functional layer having both hole injection and hole transport capabilities, an electron injection layer, an electron transport layer, or a functional layer having both electron injection and electron transport capabilities.

When the organic layer, including the heterocyclic compound of Formula 1, is an emission layer, the heterocyclic compound of Formula 1 may be used as a host or dopant for a fluorescent or phosphorescent device.

In some embodiments, the organic layer of the organic light-emitting device may include an emission layer, a hole transport layer, and/or an electron transport layer. When the first layer is an emission layer, a hole transport layer, and/or an electron transport layer, the emission layer may further include an anthracene compound, an arylamine compound, or a styryl compound.

At least one hydrogen atom in the anthracene, arylamine, or styryl compound may be substituted with a substituent described above in conjunction with the $C_1$-$C_{60}$ alkyl group.

The arylamine refers to a $C_5$-$C_{50}$ arylamine group.

In some embodiments, the organic layer of the organic light-emitting device may include an emission layer, a hole transport layer, and/or an electron transport layer. When the first layer is an emission layer, a hole transport layer, and/or an electron transport layer, either one of the red, green, blue, and white layers of the emission layer may further include a suitable phosphorescent compound.

In some embodiments, the organic layer of the organic light-emitting device may further include, but not limited to, a hole injection layer, a hole transport layer, a functional layer having both hole injection and hole transport capabilities, an emission layer, a hole blocking layer, an electron transport layer, an electron injection layer, or a combination of at least two thereof. At least one of the hole injection layer, the hole transport layer, and the functional layer having both hole injection and hole transport capabilities may further include a charge generating material for improved layer conductivity, in addition to the heterocyclic compound of Formula 1 described above, a suitable hole injection material, and a suitable hole transport material.

The charge generating material may include, for example, a p-dopant. Non-limiting examples of the p-dopant include quinone derivatives such as tetracyanoquinonedimethane (TCNQ), 2,3,5,6-tetrafluoro-tetracyano-1,4-benzoquinonedimethane (F4TCNQ), and the like; metal oxides such as tungsten oxide, molybdenum oxide, and the like; and cyano-containing compounds such as Compound 100 below.

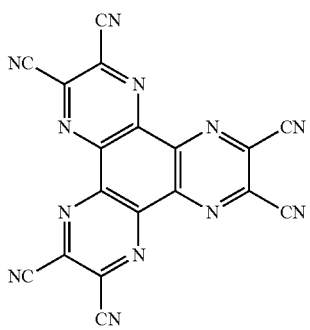

Compound 100

When the hole injection layer, the hole transport layer, or the functional layer having both hole injection and hole transport capabilities further includes a charge generating material, the charge generating material may be uniformly dispersed or nonuniformly distributed in the layer.

In some embodiments the electron transport layer of the organic light-emitting device may further include an electron-transporting organic compound and a metal-containing material. Non-limiting examples of the electron-transporting organic compound include 9,10-di(naphthalen-2-yl)anthracene (ADN), and anthracene-based compounds, such as Compounds 101 and 102 below.

Compound 101

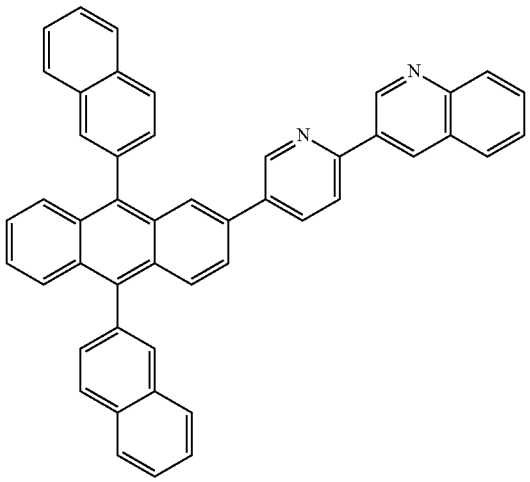

Compound 102

The metal-containing material may include a lithium (Li) complex. Non-limiting examples of the Li complex include lithium quinolate (LiQ), Compound 103 below, and the like:

Compound 103

The first electrode may be an anode, and the second electrode may be a cathode, but the reverse is also possible.

In some embodiments, the organic light-emitting device may have a first electrode/hole injection layer/emission layer/second electrode structure, a first electrode/hole injection layer/hole transport layer/emission layer/electron transport layer/second electrode structure, or a first electrode/hole injection layer/hole transport layer/emission layer/electron transport layer/electron injection layer/second electrode structure. In some other embodiments, the organic light-emitting device may have a first electrode/functional layer (having both hole injection and hole transport capabilities)/emission layer/electron transport layer/second electrode structure, or a first electrode/functional layer (having both hole injection and hole transport capabilities)/emission layer/electron transport layer/electron injection layer/second electrode structure. Alternatively, the organic light-emitting device may have a first electrode/hole transport layer/emission layer/functional layer (having both electron injection and electron transport capabilities)/second electrode structure, a first electrode/hole injection layer/emission layer/functional layer (having both electron injection and electron transport capabilities)/second electrode structure, or a first electrode/hole injection layer/hole transport layer/emission layer/functional layer (having both electron injection and electron transport capabilities)/second electrode structure.

According to some embodiments, the organic light-emitting device may be either a top-emission organic light-emitting device or a bottom-emission organic light-emitting device.

Hereinafter, a method of manufacturing an organic light-emitting device according to an embodiment of the present invention will be described with reference to the attached drawing. Here, the attached drawing illustrates the structure of an organic light-emitting device according to an embodiment of the present invention. Referring to the attached drawing, the organic light-emitting device according to the present embodiment includes a substrate (not shown), a first electrode (anode), a hole injection layer (HIL), a hole transport layer (HTL), an emission layer (EML), an electron transport layer (ETL), an electron injection layer (EIL), and a second electrode (cathode).

First, the first electrode is formed on the substrate by using a deposition or sputtering method. The first electrode may be formed of a first electrode material having a high work function. The first electrode may constitute an anode or a cathode. The substrate may be a suitable substrate used in organic light-emitting devices, and may include, for example, a glass substrate or a transparent plastic substrate with excellent mechanical strength, thermal stability, transparency, surface smoothness, ease of handling, and water resistance. Examples of the first electrode material include materials, such as indium tin oxide (ITO), indium zinc oxide (IZO), tin oxide ($SnO_2$), zinc oxide (ZnO), aluminum (Al), silver (Ag), and magnesium (Mg), which have excellent conductivity. The first electrode may be formed as a transparent or reflective electrode.

Next, the HIL may be formed on the first electrode using various methods, for example, by vacuum deposition, spin coating, casting, Langmuir-Blodgett (LB) deposition, or the like.

When the HIL is formed using vacuum deposition, the deposition conditions may vary according to a material that is used to form the HIL, and the structure and thermal characteristics of the HIL. For example, the deposition conditions may include a deposition temperature of about 100° C. to about 500° C., a vacuum pressure of about $10^{-8}$ torr to about $10^{-3}$ torr, and a deposition rate of about 0.01 Å/sec to about 100 Å/sec.

When the HIL is formed using spin coating, coating conditions may vary according to the material used to form the HIL, and the structure and thermal properties of the HIL. For example, the coating conditions may include a coating speed of about 2000 rpm to about 5000 rpm, and a thermal treatment temperature of about 80° C. to about 200° C. at which the solvent remaining after coating may be removed.

The HIL may be formed of the heterocyclic compound of Formula 1 or any suitable material that is commonly used to form an HIL. Non-limiting examples of the material that can be used to form the HIL include a phthalocyanine compound such as copperphthalocyanine, 4,4',4"-tris(3-methylphenylphenylamino)triphenylamine (m-MTDATA), N,N'-di(1-naphthyl)-N,N'-diphenylbenzidine (NPB), TDATA, 2T-NATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and polyaniline)/poly(4-styrenesulfonate (PANI/PSS).

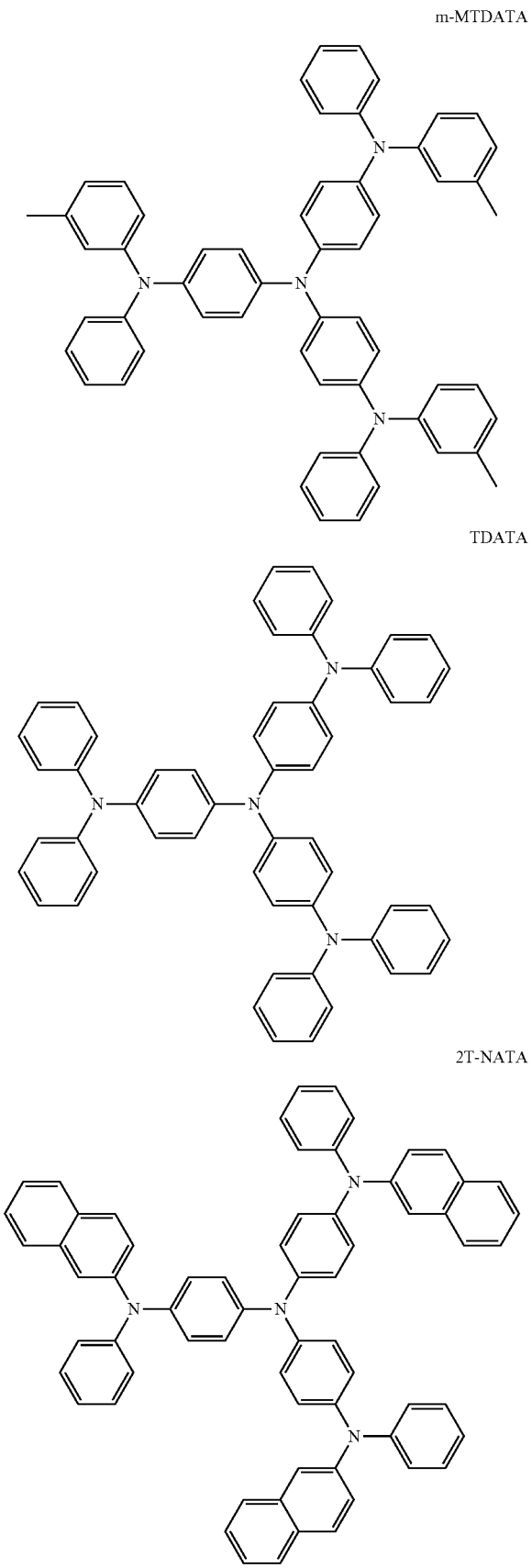

The HIL may have a thickness of about 100 Å to about 10000 Å, for example, a thickness of about 100 Å to about 1000 Å. When the thickness of the HIL is within these ranges, the HIL may have good hole injection characteristics without an increase in driving voltage.

Next, the HTL may be formed on the HIL using various methods, for example, vacuum deposition, spin coating, casting, LB deposition, or the like. When the HTL is formed using vacuum deposition or spin coating, the deposition or coating conditions may be similar to those applied to form the HIL, though the deposition or coating conditions may vary according to the material that is used to form the HTL.

The HTL may be formed of the heterocyclic compound of Formula 1 or any suitable HTL material. Non-limiting examples of such HTL materials include carbazole derivatives such as N-phenylcarbazole or polyvinylcarbazole, and amine derivatives having an aromatic condensed ring, such as NPB, N,N'-bis(3-methylphenyl)-N,N"-diphenyl-[1,1-biphenyl]-4,4'-diamine (TPD).

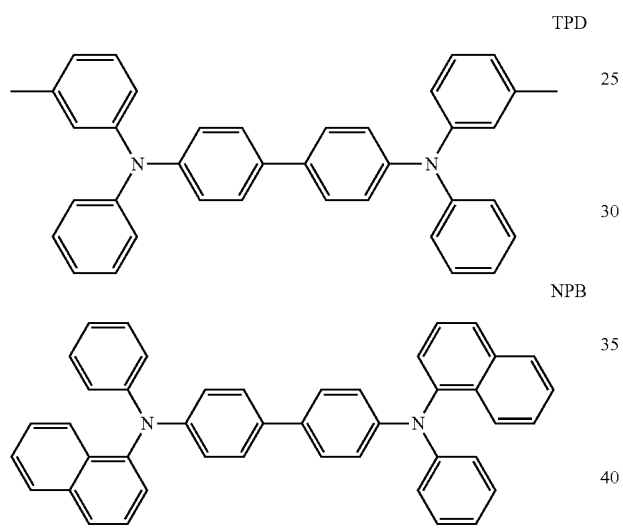

TPD

NPB

The HTL may have a thickness of about 50 Å to about 1000 Å, for example, a thickness of about 100 Å to about 600 Å. When the thickness of the HTL is within these ranges, the HTL may have good hole transport characteristics without a substantial increase in driving voltage.

Next, the EML may be formed on the HTL using various methods, for example, by vacuum deposition, spin coating, casting, LB deposition, or the like. When the EML is formed using vacuum deposition or spin coating, the deposition or coating conditions may be similar to those applied to form the HIL, though the deposition or coating conditions may vary according to the material that is used to form the EML.

The EML may include the heterocyclic compound of Formula 1 described above. For example, the heterocyclic compound of Formula 1 may be used as a host or a dopant. The EML may be formed using a variety of well-known light-emitting materials, in addition to the heterocyclic compound of Formula 1. Alternatively, the EML may also be formed using a suitable host and a suitable dopant. Dopants that may be used to form the EML may include either a fluorescent dopant or a phosphorescent dopant which are known in the art.

Examples of the host include Alq3, 4,4'-N,N'-dicarbazole-biphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di-2-naphthylanthracene (TBADN), E3, and distyrylarylene (DSA), but are not limited thereto.

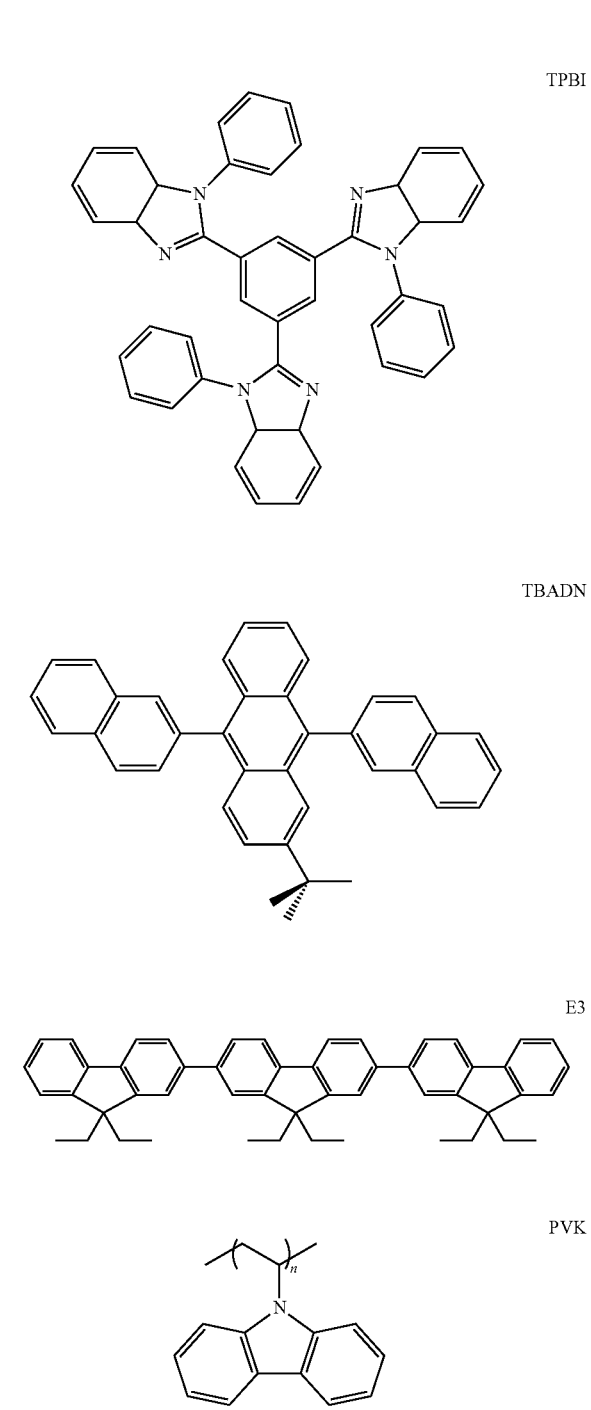

TPBI

TBADN

E3

PVK

Examples of red dopants include, but are not limited to, platinum(II) octaethylporphyrin (PtOEP), Ir(piq)$_3$, Btp$_2$Ir(acac), and DCJTB.

PtOEP

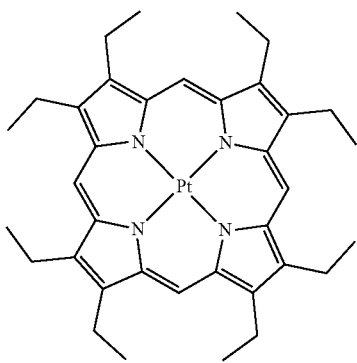

Ir(piq)₃

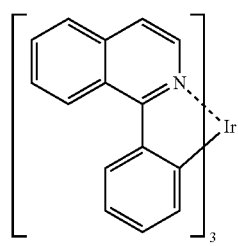

Btp₂Ir(acac)

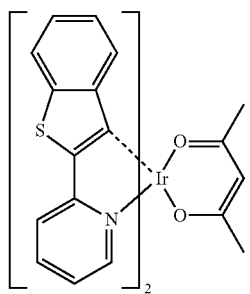

Examples of green dopants may include, but are not limited to, Ir(ppy)₃ (where "ppy" denotes phenylpyridine), Ir(ppy)₂(acac), Ir(mpyp)₃, and C545T.

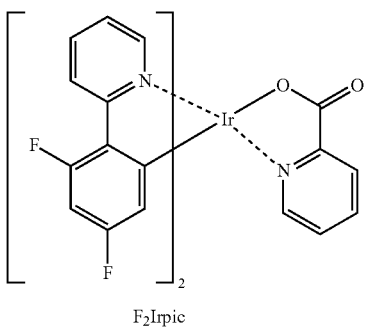

F₂Irpic

Ir(ppy)₃

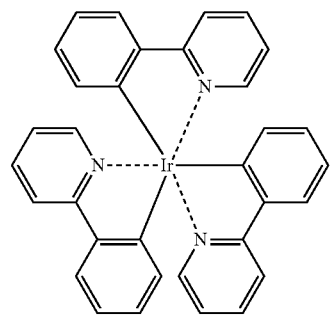

Ir(ppy)₂(acac)

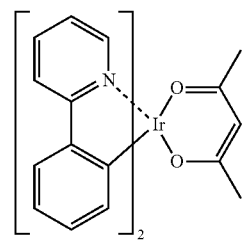

Ir(mpyp)₃

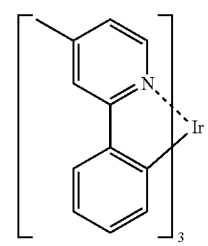

C545T

Non-limiting examples of blue dopants include the heterocyclic compound of Formula 1, F₂Irpic, (F₂ ppy)₂Ir(tmd), Ir(dfppz)₃, ter-fluorene, 4,4'-bis(4-diphenylaminostyryl)biphenyl (DPAVBi), and 2,5,8,11-tetra-t-butyl phenylene (TBP).

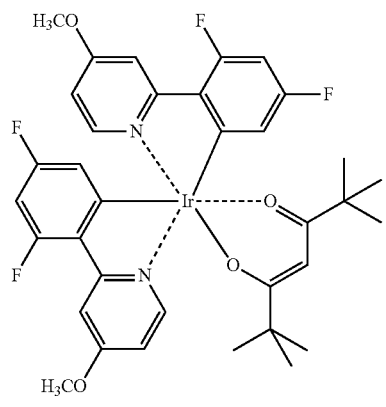

(F₂ppy)₂Ir(tmd)

-continued

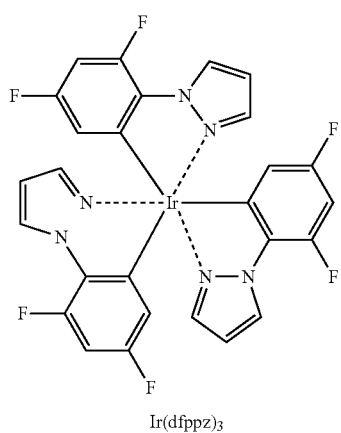

Ir(dfppz)₃

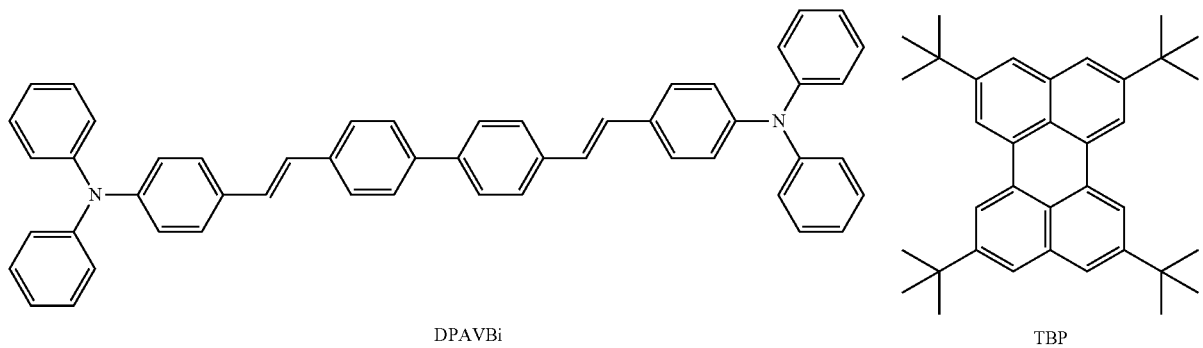

DPAVBi                                         TBP

The amount of the dopant may be from about 0.1 to about 20 parts by weight, and in some other embodiments, may be from about 0.5 to about 12 parts by weight, based on 100 parts by weight of the EML material, which is equivalent to the total weight of the host and the dopant. When the amount of the dopant is within these ranges, concentration quenching may be substantially prevented.

The EML may have a thickness of about 100 Å to about 1,000 Å, for example, about 200 Å to about 600 Å. When the thickness of the EML is within these ranges, the EML may have good light-emitting characteristics without a substantial increase in driving voltage.

When the EML includes a phosphorescent dopant, a hole blocking layer (HBL, not shown in FIG. 1) may be formed on the EML in order to prevent diffusion of triplet excitons or holes into the ETL. In this case, the HBL may be formed of any material commonly used to form an HBL. Non-limiting examples of such HBL materials include oxadiazole derivatives, triazole derivatives, phenathroline derivatives, Balq, and BCP.

The HBL may have a thickness of about 50 Å to about 1,000 Å, for example, about 100 Å to about 300 Å. When the thickness of the HBL is within these ranges, the HBL may have good hole blocking characteristics without a substantial increase in driving voltage.

Next, the ETL is formed on the EML (or HBL) using various methods, for example, by vacuum deposition, spin coating, casting, or the like. When the ETL is formed using vacuum deposition or spin coating, the deposition or coating conditions may be similar to those applied to form the HIL, though the deposition or coating conditions may vary according to the material that is used to form the ETL.

The ETL material may include the heterocyclic compound of Formula 1 described above. Alternatively, the ETL may be formed of any suitable material. Non-limiting examples of the ETL material include quinoline derivatives, such as tris (8-quinolinolate)aluminum (Alq3), TAZ, and BAIq.

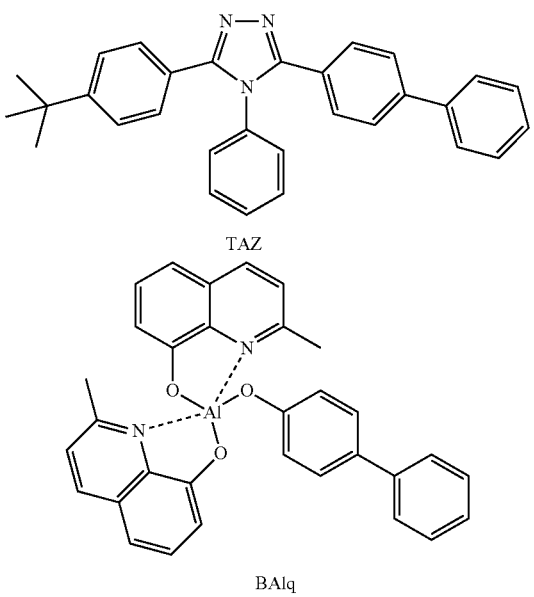

TAZ

BAlq

The ETL may have a thickness of about 100 Å to about 1,000 Å, for example, about 100 Å to about 500 Å. When the thickness of the ETL is within these ranges, the ETL may have good electron transport characteristics without a substantial increase in driving voltage.

In addition, the EIL, which facilitates injection of electrons from the cathode, may be formed on the ETL.

The EIL may include the heterocyclic compound of Formula 1 described above. Alternatively, well-known EIL materials, such as LiF, NaCl, CsF, Li$_2$O, or BaO, may be used to form the EIL. The deposition or coating conditions may be similar to those applied to form the HIL, although the deposition and coating conditions may vary according to the material that is used to form the EIL.

The EIL may have a thickness of about 1 Å to about 100 Å, for example, about 5 Å to about 90 Å. When the thickness of the EIL is within these ranges, the EIL may have good electron injection characteristics without a substantial increase in driving voltage.

Finally, the second electrode may be formed on the EIL by using, for example, vacuum deposition, sputtering, or the like. The second electrode may constitute a cathode or an anode. The material for forming the second electrode may include a metal, an alloy, or an electrically conductive compound, which are materials having a low work function, or a mixture thereof. Examples of such materials include, but are not limited to, lithium (Li), magnesium (Mg), aluminum (Al), aluminum-lithium (Al—Li), calcium (Ca), magnesium-indium (Mg—In), and magnesium-silver (Mg—Ag). In addition, in order to manufacture a top-emission organic light-emitting device, a transparent cathode formed of a transparent material such as ITO or IZO may be used as the second electrode.

According to embodiments, the organic light-emitting device may include a plurality of organic layers, wherein at least one of the organic layers may be formed of the heterocyclic compound of Formula 1 by using a deposition method or a wet method of coating a solution of the heterocyclic compound of Formula 1.

According to embodiments, the organic light-emitting device may be included in various types of flat panel display devices, such as in a passive matrix organic light-emitting display device or in an active matrix organic light-emitting display device. In particular, when the organic light-emitting device is included in an active matrix organic light-emitting display device including a thin-film transistor, the first electrode on the substrate may function as a pixel electrode, electrically connected to a source electrode or a drain electrode of the thin-film transistor. Moreover, the organic light-emitting device may also be included in flat panel display devices having double-sided screens.

Hereinafter, the present invention will be described in detail with reference to synthesis examples of Compounds 3, 5, 11, 18, 23, 39, and 41 and other examples. However, these examples are for illustrative purposes only and are not intended to limit the scope of the present invention.

EXAMPLES

Synthesis Example 1

Synthesis of Compound 3

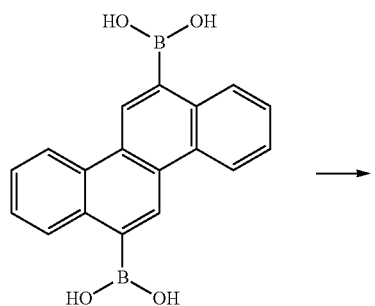

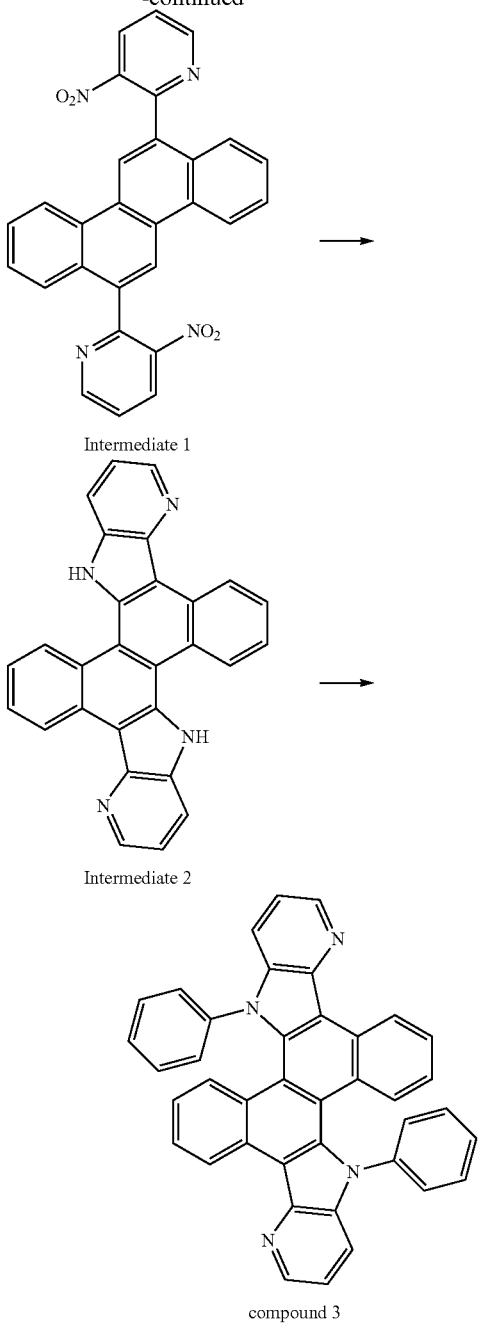

Intermediate 1

Intermediate 2 compound 3

Synthesis of Intermediate 1

6.31 g (20.0 mmol) of 6,12-chrysenediboronic acid, 8.12 g (40.0 mmol) of 2-bromo-3-nitropyridine, 1.15 g (1.0 mmol) of Pd(PPh3)4, and 8.29 g (60.0 mmol) of K2CO3 were dissolved in 60 mL of a mixed tetrahydrofuran (THF) and H2O (2:1) solution to obtain a reaction solution, which was then stirred at about 70° C. for about 5 hours. The reaction solution was cooled to room temperature, and 40 mL of water was added thereto, followed by three times of extraction with 50 mL of ethylether. The organic phase was collected, and then dried using magnesium sulfate to evaporate the solvent. The residue was separated and purified using silica gel column chromatography to obtain 8.7 g of Intermediate 1 (Yield:

92%). This compound was identified using liquid chromatography-mass spectroscopy (LC-MS) and nuclear magnetic resonance (NMR). $C_{23}H_{16}N_4O_4$: M+472.5

Synthesis of Intermediate 2

4.72 g (10.0 mmol) of Intermediate 1 and 11.54 g (44 mmol) of triphenylphosphine (PPh$_3$) were dissolved in 30 mL of 1,2-dichlorobenzene to obtain a solution, which was then stirred at about 170° C. for about 12 hours. The reaction solution was cooled to room temperature, and the solvent was removed therefrom under vacuum conditions, followed by three times of extraction with 50 mL of water and 50 mL of dichloromethane. The organic phase was collected and then dried using magnesium sulfate to evaporate the solvent. The residue was separated and purified using silica gel column chromatography to obtain 2.65 g of Intermediate 2 (Yield: 65%). This compound was identified using LC-MS and NMR. $C_{28}H_{16}N_4$: M+408.5

Synthesis of Compound 3

4.08 g (10.0 mmol) of Intermediate 2, 4.08 g (20.0 mmol) of iodobenzene, 0.19 g (1.0 mmol) of CuI, 0.05 g (0.2 mmol) of 18-Crown-6, and 4.15 g (30.0 mmol) of K2CO3 were dissolved in 30 mL of 1,3-dimethyl-3,4,5,6-tetrahydro-2 (1H)-pyrimidinone (DMPU) to obtain a solution, which was then stirred at about 170° C. for about 12 hours. The reaction solution was cooled to room temperature, followed by three times of extraction with 50 mL of water and 50 mL of dichloromethane. The organic phase was collected and then dried using magnesium sulfate to evaporate the solvent. The residue was separated and purified using silica gel column chromatography to obtain 4.26 g of Compound 3 (Yield: 76%). This compound was identified using LC-MS and NMR. ($^1$H NMR (CDCl$_3$, 400 MHz) δ (ppm) 8.62-8.22 (d, 2H), 8.52-8.51 (d, 2H), 8.22-8.20 (d, 2H), 7.90-7.86 (t, 2H), 7.67-7.65 (d, 2H), 7.60-7.55 (m, 8H), 7.38-7.31 (m, 2H), 7.05-7.02 (m, 2H), 6.95-6.93 (t, 2H)) $C_{40}H_{24}N_4$: M+560.7

Synthesis Example 2

Synthesis of Compound 5

5.42 g of Compound 5 was synthesized from 2-iodo-naphthalene, instead of iodobenzene, in the same manner as in the synthesis of Compound 3 (Yield: 82%). This compound was identified using LC-MS and NMR. ($^1$H NMR (CDCl$_3$, 400 MHz) δ (ppm) 8.62-8.60 (d, 2H), 8.52-8.51 (d, 2H), 8.22-8.20 (d, 2H), 8.02-8.01 (d, 2H), 7.90-7.86 (m, 4H), 7.77-7.72 (m, 2H), 7.66-7.63 (m, 4H), 7.58-7.49 (m, 6H), 7.05-7.02 (m, 2H), 6.97-6.93 (t, 2H)) $C_{48}H_{28}N_4$: M+660.8

Synthesis Example 3

Synthesis of Compound 11

6.26 g of Compound 11 was synthesized from 2-bromo-9,9-dimethylfluorene, instead of iodobenzene, in the same manner as in the synthesis of Compound 3 (Yield: 79%). This compound was identified using LC-MS and NMR. ($^1$H NMR (CDCl$_3$, 400 MHz) δ (ppm) 8.74-8.72 (d, 2H), 8.69 (s, 2H), 8.62-8.60 (d, 2H), 8.52-8.51 (d, 2H), 8.22-8.20 (d, 2H), 8.16-8.14 (d, 4H), 7.90-7.80 (m, 4H), 7.65-7.63 (d, 2H), 7.52-7.41 (m, 7H), 7.17-7.11 (m, 7H), 7.04-7.01 (m, 2H), 6.97-6.93 (t, 2H), 6.85-6.83 (d, 2H)) $C_{58}H_{40}N_4$: M+793.0

Synthesis Example 4

Synthesis of Compound 18

6.41 g of Compound 18 was synthesized from 3-bromo-9-phenylcarbazole, instead of iodobenzene, in the same manner as in the synthesis of Compound 3 (Yield: 72%). This compound was identified using LC-MS and NMR. ($^1$H NMR (CDCl$_3$, 400 MHz) δ (ppm) 8.62-8.60 (d, 2H), 8.52-8.51 (d, 2H), 8.22-8.20 (d, 2H), 8.13-8.11 (m, 4H), 7.90-7.86 (t, 2H), 7.67-7.65 (d, 2H), 7.59-7.57 (d, 2H), 7.52-7.46 (d, 8H), 7.36-7.30 (m, 8H), 7.13-7.11 (d, 2H), 7.05-7.02 (m, 2H), 6.95-6.93 (t, 2H)) $C_{64}H_{38}N_6$: M+891.0

Synthesis Example 5

Synthesis of Compound 23

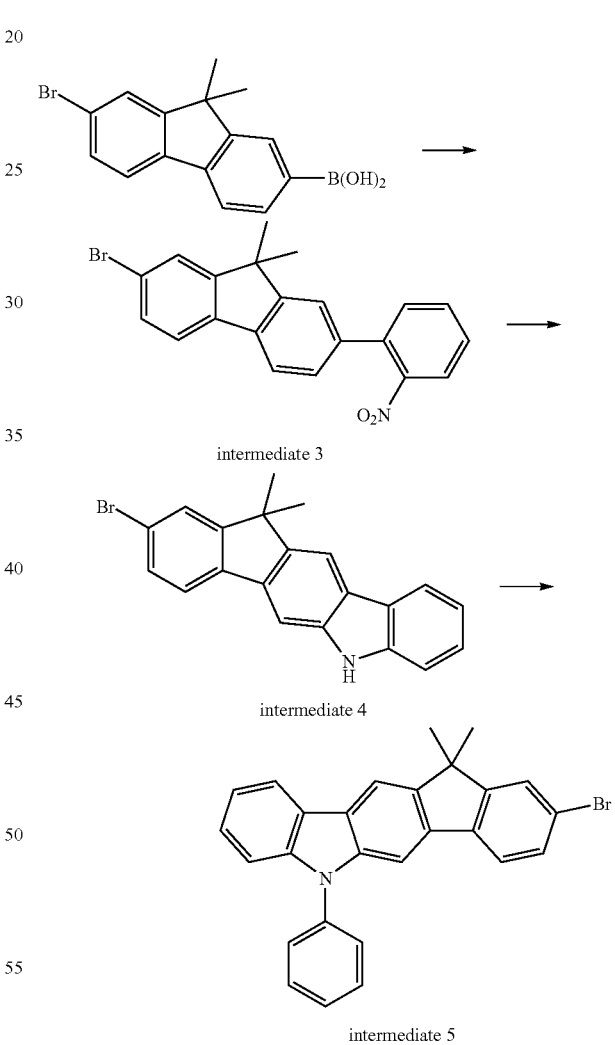

intermediate 3 intermediate 4 intermediate 5

Synthesis of Intermediate 3

6.34 g (20.0 mmol) of 2-bromo-9,9-dimethyl-7-fluoreneboronic acid, 4.04 g (20.0 mmol) of 2-bromonitrobenzene, 1.15 g (1.0 mmol) of Pd(PPh3)4, and 8.29 g (60.0 mmol) of K$_2$CO$_3$ were dissolved in 60 mL of a mixed tetrahydrofuran (THF) and H2O (2:1) solution to obtain a solution, which was then stirred at about 70° C. for about 5 hours. The reaction solution was cooled to room temperature, and 40 mL of water was added thereto, followed by three times of extraction with 50 mL of ethylether. The organic phase was collected and then dried using magnesium sulfate to evaporate the solvent. The residue was separated and purified using silica gel column chromatography to obtain 6.86 g of Intermediate 3 (Yield: 87%). This compound was identified using LC-MS. $C_{21}H_{16}BrNO_2$: M+393.0

Synthesis of Intermediate 4

3.94 g (10.0 mmol) of Intermediate 3 and 5.77 g (22 mmol) of triphenylphosphine (PPh$_3$) were dissolved in 30 mL of 1,2-dichlorobenzene to obtain a solution, which was then stirred at about 170° C. for about 12 hours. The reaction solution was cooled to room temperature, and the solvent was removed therefrom under vacuum conditions, followed by three times of extraction with 50 mL of water and 50 mL of dichloromethane. The organic phase was collected and then dried using magnesium sulfate to evaporate the solvent. The residue was separated and purified using silica gel column chromatography to obtain 2.83 g of Intermediate 4 (Yield: 78%). This compound was identified using LC-MS. $C_{21}H_{16}BrN$: M+361.0

Synthesis of Intermediate 5

3.62 g (10.0 mmol) of Intermediate 4, 3.06 g (15.0 mmol) of iodobenzene, 0.19 g (1.0 mmol) of CuI, 0.05 g (0.2 mmol) of 18-Crown-6, and 4.15 g (30.0 mmol) of K$_2$CO$_3$ were dissolved in 30 mL of 1,3-dimethyl-3,4,5,6-tetrahydro-2(1H)-pyrimidinone (DMPU) to obtain a solution, which was then stirred at about 170° C. for about 12 hours. The reaction solution was cooled to room temperature, followed by three times of extraction with 50 mL of water and 50 mL of dichloromethane. The organic phase was collected and then dried using magnesium sulfate to evaporate the solvent. The residue was separated and purified using silica gel column chromatography to obtain 4.03 g of Intermediate 5 (Yield: 92%). This compound was identified using LC-MS. $C_{27}H_{20}BrN$: M+437.1

Synthesis of Compound 23

8.42 g of Compound 23 was synthesized from Intermediate 5, instead of iodobenzene, in the same manner as in the synthesis of Compound 3 (Yield: 75%). This compound was identified using LC-MS and NMR. ($^1$H NMR (CDCl$_3$, 400 MHz) δ (ppm) 8.62-8.60 (d, 2H), 8.52-8.51 (d, 2H), 8.22-8.20 (d, 2H), 8.06-8.03 (m, 2H), 7.98-7.96 (d, 2H), 7.93-7.86 (m, 4H), 7.77-7.75 (d, 2H), 7.65-7.63 (d, 2H), 7.49-7.43 (m, 8H), 7.36-7.26 (m, 8H), 7.05-7.03 (m, 2H), 6.97-6.93 (t, 2H), 6.86 (s, 2H), 6.60-6.58 (d, 2H), 2.03 (s, 12H)) $C_{82}H_{54}N_6$: M+1123.4

Synthesis Example 6

Synthesis of Compound 39

5.91 g of Compound 39 was synthesized from 4-bromotriphenylamine, instead of iodobenzene, in the same manner as in the synthesis of Compound 3 (Yield: 66%). This compound was identified using liquid LC-MS and NMR. ($^1$H NMR (CDCl$_3$, 400 MHz) δ (ppm) 8.62-8.60 (d, 2H), 8.51 (d, 2H), 8.22-8.20 (d, 2H), 7.93-7.86 (m, 6H), 7.67-7.65 (d, 2H), 7.33-7.31 (m, 8H), 7.05-7.02 (m, 2H), 6.95-6.93 (t, 2H), 6.74-6.70 (m, 4H), 6.33-6.31 (d, 4H), 6.10-6.08 (d, 8H)) $C_{64}H_{42}N_6$: M+895.1

Synthesis Example 7

Synthesis of Compound 41

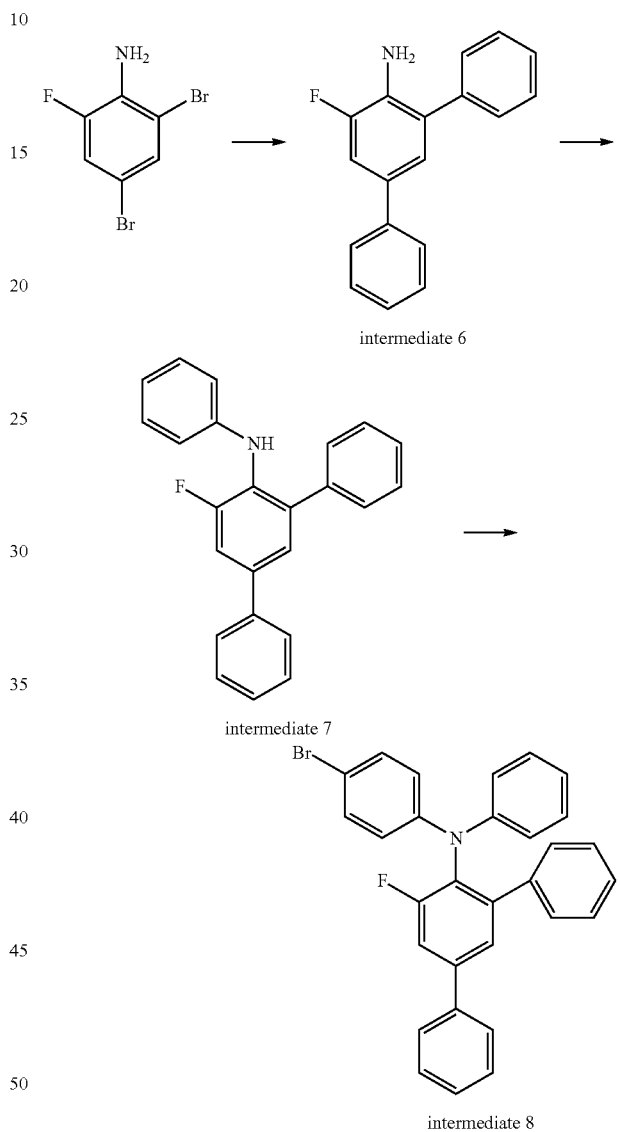

intermediate 6 intermediate 7 intermediate 8

Synthesis of Intermediate 6

5.38 g (20.0 mmol) of 2,4-dibromo-6-fluoro-phenylamine, 5.36 g (44.0 mmol) of phenylboronic acid, 1.15 g (1.0 mmol) of Pd(PPh3)4, and 8.29 g (60.0 mmol) of K2CO3 were dissolved in 80 mL of a mixed solution THF/H2O (2:1) to obtain a reaction solution, which was then stirred at about 70° C. for about 5 hours. The reaction solution was cooled to room temperature, followed by three times of extraction with 60 mL of water and 60 mL of diethylether. The organic phase was collected and then dried using magnesium sulfate to evaporate the solvent. The residue was separated and purified using silica gel column chromatography to obtain 4.11 g of Intermediate 6 (Yield: 78%). This compound was identified using LC-MS and NMR. $C_{18}H_{14}FN$: M+263.1

Synthesis of Intermediate 7

2.63 g (10.0 mmol) of Intermediate 6, 2.04 g (10.0 mmol) of iodobenzene, 1.44 g (15 mmol) of t-BuONa, 183 mg (0.2 mmol) of $Pd_2(dba)_3$, and 40 mg (0.2 mmol) of $P(t-Bu)_3$ were dissolved in 30 ml of toluene and stirred at 90° C. for 3 hours. After the reaction was completed, the reaction product was cooled to room temperature and extracted three times with distilled water and 50 ml of diethylether. The organic phase was collected, and was dried using magnesium sulfate to evaporate the solvent. The residue was separated and purified using silica gel column chromatography to obtain 2.54 g of Intermediate 7 (Yield: 75%). This compound was identified using HR-MS. $C_{24}H_{18}FN$: M+339.4

Synthesis of Intermediate 8

3.39 g (10.0 mmol) of Intermediate 7, 4.24 g (15.0 mmol) of 4-bromoiodobenzene, 0.18 g (0.2 mmol) of Pd2(dba)3, and 0.04 g (0.4 mmol) of $P(t-Bu)_3$, and 1.44 g (15 mmol) of t-BuONa were dissolved in 40 mL of toluene to obtain a mixture, which was then stirred at about 85° C. for 4 hours. The reaction solution was cooled to room temperature, followed by three times of extraction with 30 mL of water and 30 mL of diethylether. The organic phase was collected and then dried using magnesium sulfate to evaporate the solvent. The residue was separated and purified using silica gel column chromatography to obtain 2.38 g of Intermediate 5 (Yield: 63%). This compound was identified using LC-MS and NMR. 3.31 g of Intermediate 8 was obtained with a yield of 67%. This compound was identified using liquid LC-MS and NMR. $C_{30}H_{21}BrFN$: M+494.4

Synthesis of Compound 41

8.23 g of Compound 41 was synthesized from Intermediate 8, instead of iodobenzene, in the same manner as in the synthesis of Compound 3 (Yield: 71%). This compound was identified using LC-MS and NMR. ($^1$H NMR (CDCl$_3$, 400 MHz) δ (ppm) 8.93 (d, 2H), 8.62-8.60 (d, 2H), 8.52 (d, 2H), 8.22-8.20 (d, 2H), 7.92-7.87 (m, 10H), 7.81-7.79 (t, 3H), 7.67-7.65 (d, 3H), 7.48-7.44 (t, 4H), 7.30-7.26 (t, 4H), 7.14-7.09 (t, 2H), 7.05-7.03 (m, 4H), 6.95-6.93 (t, 2H), 6.77-6.73 (m, 2H), 6.64-6.60 (t, 2H), 6.48-6.46 (d, 4H), 6.25-6.23 (d, 4H)) $C_{82}H_{52}F_2N_6$: M+1189.3

Example 1

To manufacture an anode, a Corning 15 Ω/cm² (1200 Å) ITO glass substrate was cut to a size of 50 mm×50 mm×0.7 mm and then sonicated in isopropyl alcohol and pure water each for five minutes, and then cleaned by irradiation of ultraviolet rays for 30 minutes with exposure to ozone. The resulting glass substrate was loaded into a vacuum deposition device.

Then, 2-TNATA, which is an HIL material, was vacuum-deposited on the glass substrate to form a HIL having a thickness of about 600 Å. Then, 4,4'-bis[N-(1-naphthyl)-N-phenylamino]biphenyl (NPB), which is a hole transporting compound, was vacuum-deposited on the HIL to form an HTL having a thickness of about 300 Å.

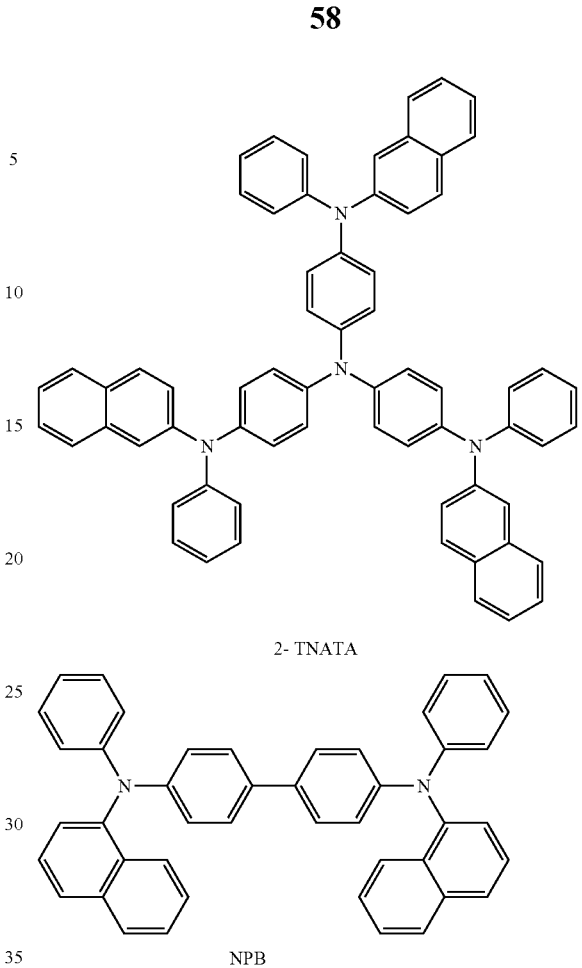

2-TNATA

NPB

Then, the Compound 3 as a green fluorescent host and a green fluorescent dopant (C545T) were simultaneously (or concurrently) deposited in a weight ratio of 98:2 on the HTL, to form an EML having a thickness of about 300 Å.

Then, Alq3 was deposited on the EML to form an ETL having a thickness of 300 Å, and then LiF, which is a halogenated alkali metal, was deposited on the ETL to form an EIL having a thickness of 10 Å. Then, Al was vacuum-deposited on the EIL to form a cathode having a thickness of 3000 Å, thereby forming an LiF/Al electrode and completing the manufacture of an organic light-emitting device.

The organic light-emitting device at a driving voltage of 6.53 V had a current density of 50 mA/cm², a high luminosity of 7,945 cd/m², a luminescent efficiency of 15.9 cd/A, and a half-lifespan of 337 hours at 100 mA/cm².

Example 2

An organic light-emitting device was manufactured in the same manner as in Example 1, except that Compound 5 was used, instead of Compound 3, to form the EML.

The organic light-emitting device at a driving voltage of 6.45 V had a current density of 50 mA/cm², a high luminosity of 8212 cd/m², a luminescent efficiency of 16.4 cd/A, and a half-lifespan of 351 hours at 100 mA/cm².

Example 3

An organic light-emitting device was manufactured in the same manner as in Example 1, except that Compound 11 was used, instead of Compound 3, to form the EML.

The organic light-emitting device at a driving voltage of 6.33 V had a current density of 50 mA/cm$^2$, a high luminosity of 9956 cd/m$^2$, a luminescent efficiency of 19.9 cd/A, and a half-lifespan of 367 hours at 100 mA/cm$^2$.

Example 4

An organic light-emitting device was manufactured in the same manner as in Example 1, except that Compound 18 was used, instead of Compound 3, to form the EML.

The organic light-emitting device at a driving voltage of 6.26 V had a current density of 50 mA/cm$^2$, a high luminosity of 9671 cd/m$^2$, a luminescent efficiency of 19.3 cd/A, and a half-lifespan of 380 hours at 100 mA/cm$^2$.

Example 5

An organic light-emitting device was manufactured in the same manner as in Example 1, except that Compound 23 was used, instead of Compound 3, to form the EML.

The organic light-emitting device at a driving voltage of 6.49 V had a current density of 50 mA/cm$^2$, a high luminosity of 8894 cd/m$^2$, a luminescent efficiency of 17.8 cd/A, and a half-lifespan of 402 hours at 100 mA/cm$^2$.

Example 6

An organic light-emitting device was manufactured in the same manner as in Example 1, except that a widely-known compound Alq$_3$ as a green fluorescent host and the Compound 39 as a green fluorescent dopant, instead of the widely-known green fluorescent dopant C545T, were used to form an EML.

The organic light-emitting device at a driving voltage of 6.38 V had a current density of 50 mA/cm$^2$, a high luminosity of 8579 cd/m$^2$, a luminescent efficiency of 17.2 cd/A, and a half-lifespan of 394 hours at 100 mA/cm$^2$.

Example 7

An organic light-emitting device was manufactured in the same manner as in Example 1, except that Compound 41 was used, instead of Compound 39 used in Example 6, to form the EML.

The organic light-emitting device at a driving voltage of 6.41 V had a current density of 50 mA/cm$^2$, a high luminosity of 9473 cd/m$^2$, a luminescent efficiency of 18.9 cd/A, and a half-lifespan of 412 hours at 100 mA/cm$^2$.

Comparative Example 1

An organic light-emitting device was manufactured in the same manner as in Example 1, except that the green fluorescent host Alq$_3$ was used, instead of Compound 3, to form the EML.

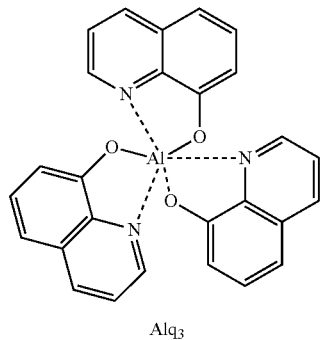

Alq$_3$

The organic light-emitting device at a driving voltage of 7.45 V had a current density of 50 mA/cm$^2$, a high luminosity of 6102 cd/m$^2$, a luminescent efficiency of 12.2 cd/A, and a half-lifespan of 237 hours at 100 mA/cm$^2$.

The organic light-emitting devices manufactured using the heterocyclic compounds of Formula 1 according to the present invention as a host or dopant material of the EML had a lower driving voltage than the light-emitting device of Comparative Example 1 manufactured using a widely-known material, and thus had higher efficiency and good I-V-L characteristics. In particular, lifetime characteristics (half lifespan) were markedly improved in the organic light-emitting devices of Examples 1-7, as compared with the organic light-emitting device of Comparative Example 1. The results are shown in Table 1 below.

TABLE 1

| | Light-emitting material | Driving voltage (V) | Current density (mA/cm$^2$) | Luminance (cd/m$^2$) | Efficiency | Emission color | Half life-span (hr @100 mA/cm$^2$) |
|---|---|---|---|---|---|---|---|
| Example 1 | Compound 3 | 6.53 | 50 | 7,945 | 15.9 | Green | 337 hr |
| Example 2 | Compound 5 | 6.45 | 50 | 8,212 | 16.4 | Green | 351 hr |
| Example 3 | Compound 11 | 6.33 | 50 | 9,956 | 19.9 | Green | 367 hr |
| Example 4 | Compound 18 | 6.26 | 50 | 9,671 | 19.3 | Green | 380 hr |
| Example 5 | Compound 23 | 6.49 | 50 | 8,894 | 17.8 | Green | 402 hr |
| Example 6 | Compound 39 | 6.38 | 50 | 8,579 | 17.2 | Green | 394 hr |
| Example 7 | Compound 41 | 6.41 | 50 | 9,473 | 18.9 | Green | 412 hr |
| Comparative Example 1 | Alq$_3$ | 7.45 | 50 | 6,102 | 12.2 | Green | 237 hr |

As described above, novel heterocyclic compounds according to the one or more of the above embodiments of the present invention have good electrical characteristics, good charge transporting capabilities, and good emission characteristics, and may be used to prevent crystallization due to having a high glass transition temperature ($T_g$). The heterocyclic compounds may also be used as electron transporting materials for most color-fluorescent and phosphorescent devices, such as red, green, blue, and white fluorescent and phosphorescent devices, or as red, green, blue, or white-light emitting materials. Thus, an organic light-emitting device with high-efficiency, low-driving voltage, high luminance, and long lifespan may be manufactured using the heterocyclic compounds.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A heterocyclic compound represented by Formula 1 below:

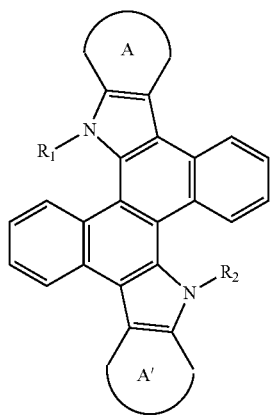

Formula 1 wherein in Formula 1, $R_1$ and $R_2$ are each independently selected from the group consisting of a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a substituted or unsubstituted $C_6$-$C_{60}$ aryloxy group, a substituted or unsubstituted $C_6$-$C_{60}$ arylthio group, a substituted or unsubstituted $C_6$-$C_{60}$ aryl group, a substituted amino group with a $C_6$-$C_{60}$ aryl or $C_3$-$C_{60}$ heteroaryl group, a substituted or unsubstituted $C_3$-$C_{60}$ heteroaryl group, a substituted or unsubstituted $C_6$-$C_{60}$ condensed polycyclic group, a halogen atom, a cyano group, a nitro group, a hydroxyl group, and a carboxyl group; and A and A' are each a substituted or unsubstituted pyridine ring.

2. The heterocyclic compound of claim 1, wherein $R_1$ and $R_2$ in Formula 1 are each independently selected from the group consisting of a hydrogen atom, a deuterium atom, a halogen atom, a cyano group, a $C_1$-$C_{40}$ alkyl group, and groups represented by formulae 2a to 2h below:

formula 2a

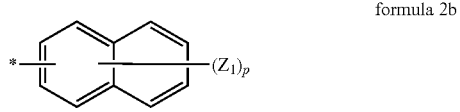

formula 2b

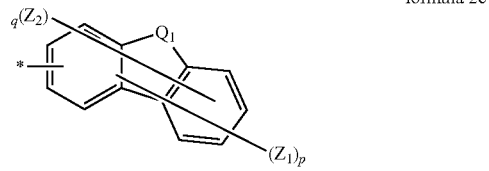

formula 2c

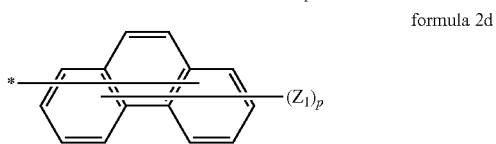

formula 2d

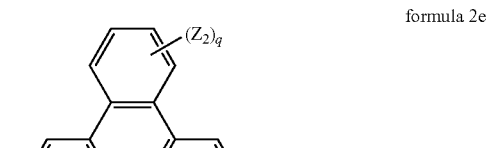

formula 2e

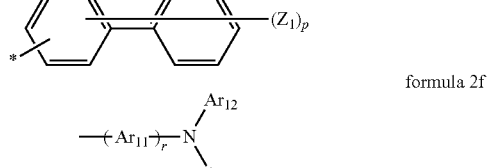

formula 2f

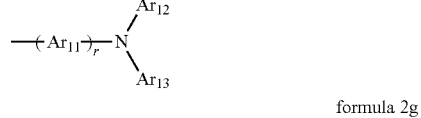

formula 2g

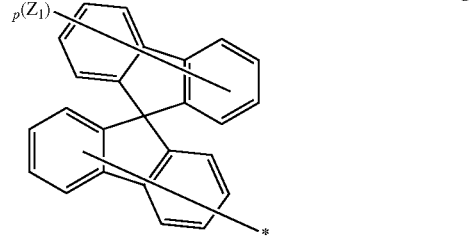

formula 2h

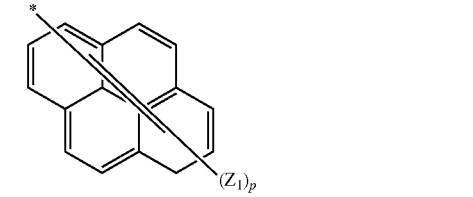

wherein, in formulae 2a to 2h, $Q_1$ is a linking group represented by —C($R_3$)($R_4$)—, —N($R_3$)—, —S—, or —O—;

$Z_1$, $Z_2$, $Ar_{12}$, $Ar_{13}$, $R_3$, and $R_4$ are each independently selected from the group consisting of a hydrogen atom, a deuterium atom, a $C_1$-$C_{20}$ alkyl group, a substituted or unsubstituted $C_6$-$C_{20}$ aryl group, a substituted or unsubstituted $C_2$-$C_{20}$ heterocyclic group, an amino group substituted with a $C_6$-$C_{20}$ aryl group or $C_3$-$C_{20}$ heteroaryl group, a cyano group, a nitro group, a hydroxyl group, and a carboxy group;

$Ar_{11}$ is a substituted or unsubstituted $C_1$-$C_{20}$ alkylene group, a substituted or unsubstituted $C_6$-$C_{20}$ arylene group, or a substituted or unsubstituted $C_2$-$C_{20}$ heterocyclic divalent group;

p is an integer from 1 to 5 in formula 2a; an integer from 1 to 7 in formulae 2b, 2c, and 2e; an integer from 1 to 12 in formulae 2g; and an integer from 1 to 9 in formulae 2d and 2h;

q is an integer from 1 to 7 in formula 2c; and an integer from 1 to 4 in formula 2e;

r is an integer from 1 to 5; and

\* indicates a respective binding site of $R_1$ and $R_2$ to a corresponding N in the heterocyclic compound of Formula 1.

3. The heterocyclic compound of claim 1, wherein $R_1$ and $R_2$ in Formula 1 are each independently selected from the group consisting of a hydrogen atom, a deuterium atom, a halogen atom, a cyano group, a methyl group, an ethyl group, a propyl group, a butyl group, a t-butyl, a pentyl group, and groups represented by formulae 3a to 3j below:

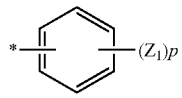

formula 3a

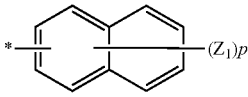

formula 3b

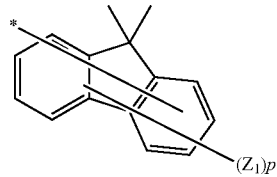

formula 3c

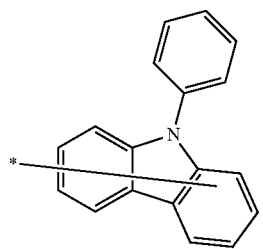

formula 3d

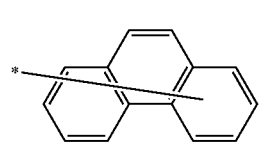

formula 3e

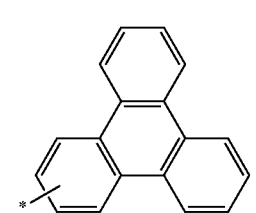

formula 3f

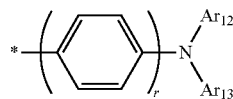

formula 3g

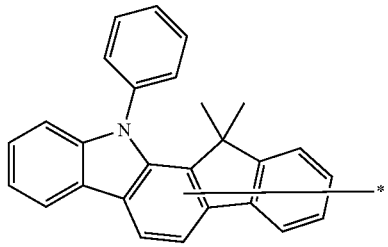

formula 3h

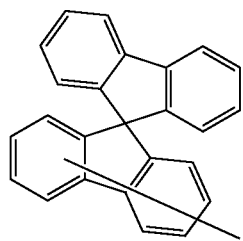

formula 3i formula 3j wherein, in formulae 3a to 3j, $Z_1$, $Ar_{12}$, and $Ar_{13}$ are each independently selected from the group consisting of a hydrogen atom, a deuterium atom, an unsubstituted $C_6$-$C_{20}$ aryl group, and a substituted or unsubstituted $C_2$-$C_{20}$ heterocyclic group;

r is an integer from 1 to 2;

p is an integer from 1 to 5; and

\* indicates a respective binding site of $R_1$ and $R_2$ to a corresponding N in the heterocyclic compound of Formula 1.

4. The heterocyclic compound of claim 1, wherein the heterocyclic compound represented by Formula 1 comprises one of the compounds represented by formula 2 to 4:

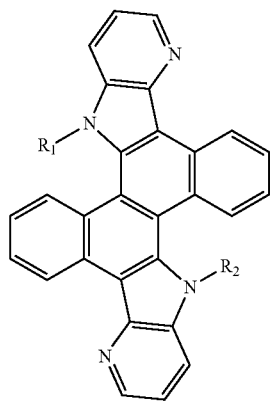

formula 2 formula 3

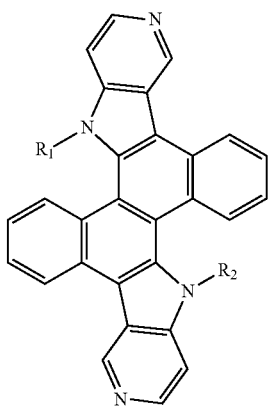

formula 3a

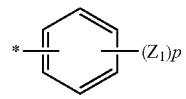

formula 3b

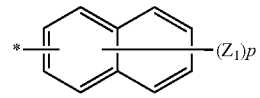

formula 3c

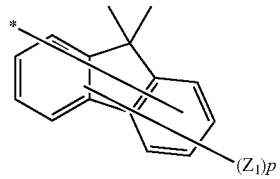

formula 4

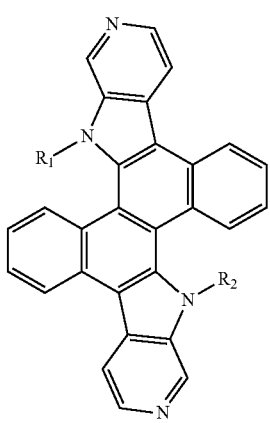

formula 3d

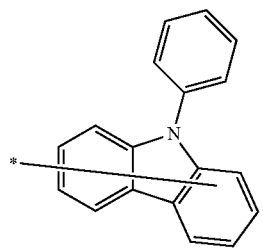

formula 3e

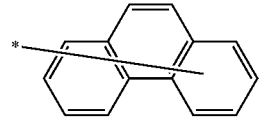

formula 3f

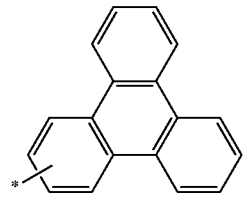

formula 3g

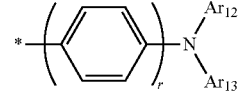

formula 3h

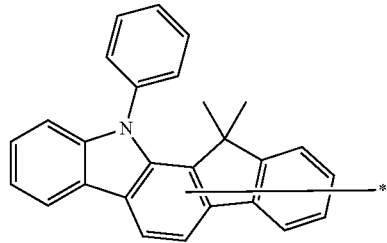

formula 3i

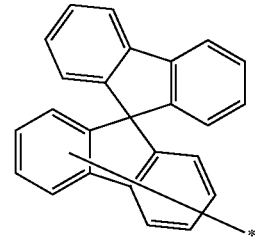

wherein, in formulae 2 to 4, $R_1$ and $R_2$ are each independently selected from the group consisting of a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a substituted or unsubstituted $C_6$-$C_{60}$ aryloxy group, a substituted or unsubstituted $C_6$-$C_{60}$ arylthio group, a substituted or unsubstituted $C_6$-$C_{60}$ aryl group, a substituted amino group with a $C_6$-$C_{60}$ aryl or $C_3$-$C_{60}$ heteroaryl group, a substituted or unsubstituted $C_3$-$C_{60}$ heteroaryl group, a substituted or unsubstituted $C_6$-$C_{60}$ condensed polycyclic group, a halogen atom, a cyano group, a nitro group, a hydroxyl group, and a carboxyl group.

5. The heterocyclic compound of claim 1, wherein $R_1$ and $R_2$ are the same.

6. The heterocyclic compound of claim 1, wherein A and A' are the same.

7. The heterocyclic compound of claim 1, wherein A and A' in Formula 1 are the same, and $R_1$ and $R_2$ are each independently selected from the group consisting of a hydrogen atom, a deuterium atom, a halogen atom, a cyano group, a methyl group, an ethyl group, a propyl group, a butyl group, a t-butyl, a pentyl group, and groups represented by formulae 3a to 3j below:

-continued formula 3j

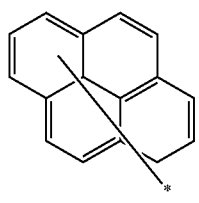

wherein, in formulae 3a to 3j, $Z_1$, $Ar_{12}$, and $Ar_{13}$ are each independently selected from the group consisting of a hydrogen atom, a deuterium atom, an unsubstituted $C_6$-$C_{20}$ aryl group, and a substituted or unsubstituted $C_2$-$C_{20}$ heterocyclic group;

r is an integer from 1 to 2;

p is an integer from 1 to 5; and

* indicates a respective binding site of $R_1$ and $R_2$ to a corresponding N in the heterocyclic compound of Formula 1.

8. The heterocyclic compound of claim 1, wherein $R_1$ and $R_2$ in Formula 1 are the same, and are selected from the group consisting of a hydrogen atom, a deuterium atom, a halogen atom, a cyano group, a methyl group, an ethyl group, a propyl group, a butyl group, a t-butyl, a pentyl group, and groups represented by formulae 3a to 3j below:

formula 3a

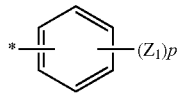

formula 3b

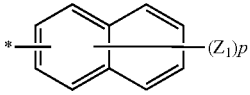

formula 3c

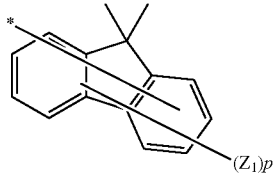

formula 3d

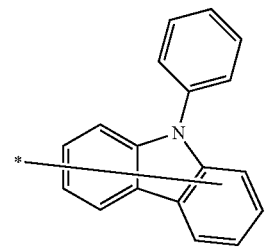

formula 3e

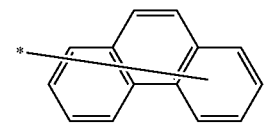

-continued formula 3f

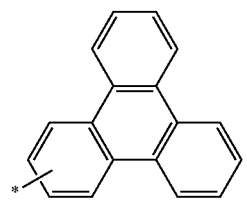

formula 3g

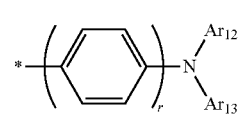

formula 3h

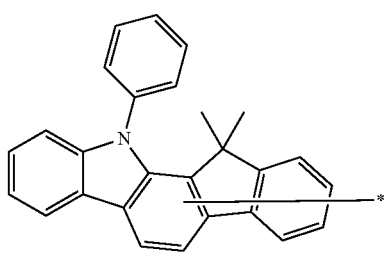

formula 3i

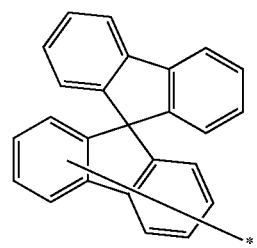

formula 3j

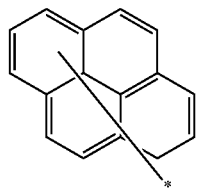

wherein, in formulae 3a to 3j, $Z_1$, $Ar_{12}$, and $Ar_{13}$ are each independently selected from the group consisting of a hydrogen atom, a deuterium atom, an unsubstituted $C_6$-$C_{20}$ aryl group, and a substituted or unsubstituted $C_2$-$C_{20}$ heterocyclic group;

r is an integer from 1 to 2;

p is an integer from 1 to 5; and

* indicates a respective binding site of $R_1$ and $R_2$ to a corresponding N in the heterocyclic compound of Formula 1.

9. The heterocyclic compound of claim 1, wherein the heterocyclic compound represented by Formula 1 comprises one of the compounds represented by formulae 2 to 4:

formula 2

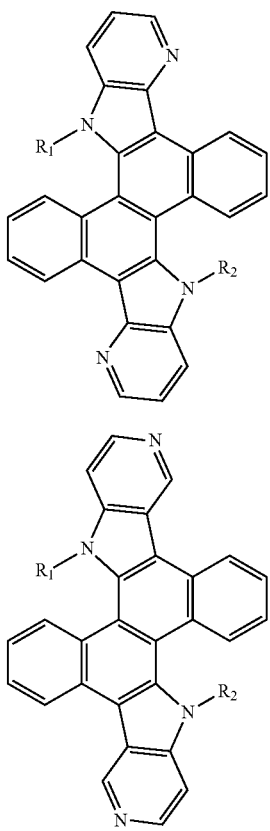

formula 3 formula 4

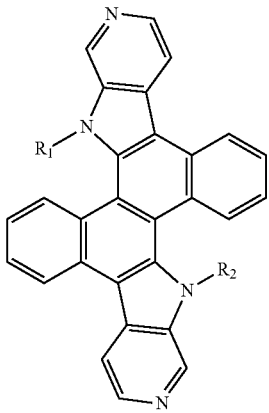

wherein, in formulae 2 to 4, $R_1$ and $R_2$ are the same, and are selected from among a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a substituted or unsubstituted $C_6$-$C_{60}$ aryloxy group, a substituted or unsubstituted $C_6$-$C_{60}$ arylthio group, a substituted or unsubstituted $C_6$-$C_{60}$ aryl group, a substituted amino group with a $C_6$-$C_{60}$ aryl or $C_3$-$C_{60}$ heteroaryl group, a substituted or unsubstituted $C_3$-$C_{60}$ heteroaryl group, a substituted or unsubstituted $C_6$-$C_{60}$ condensed polycyclic group, a halogen atom, a cyano group, a nitro group, a hydroxyl group, and a carboxyl group.

10. The heterocyclic compound of claim 1, wherein the heterocyclic compound represented by Formula 1 comprises one of the compounds below:

3

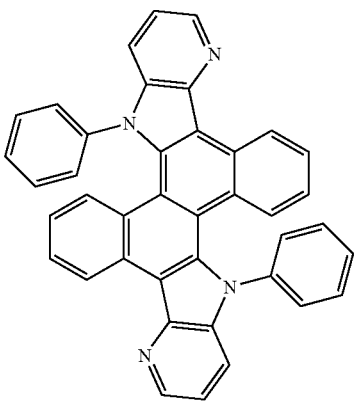

5

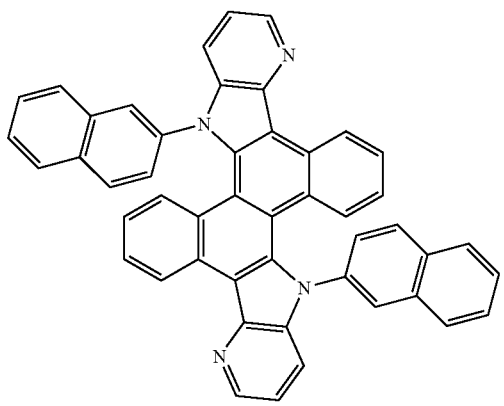

11
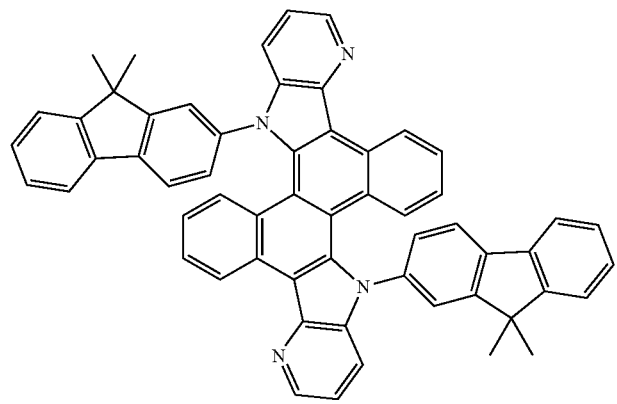
18
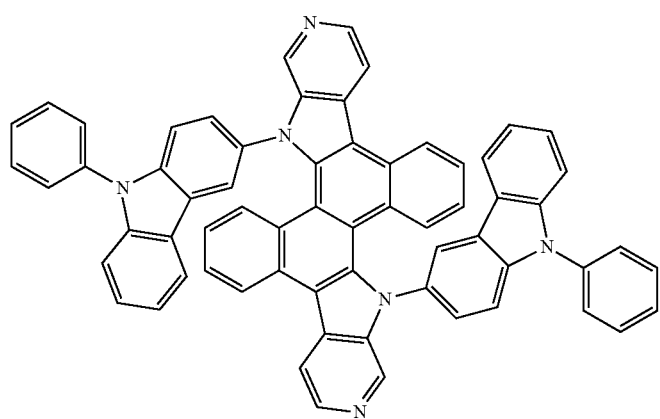
23
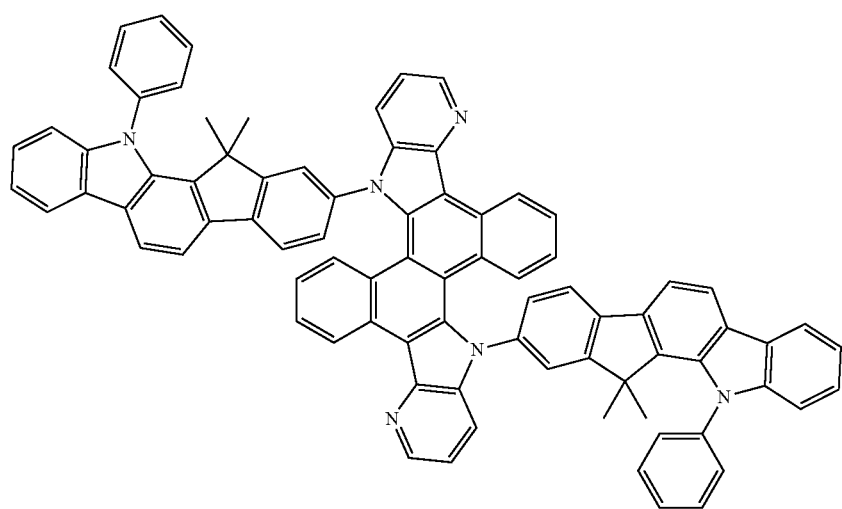

39

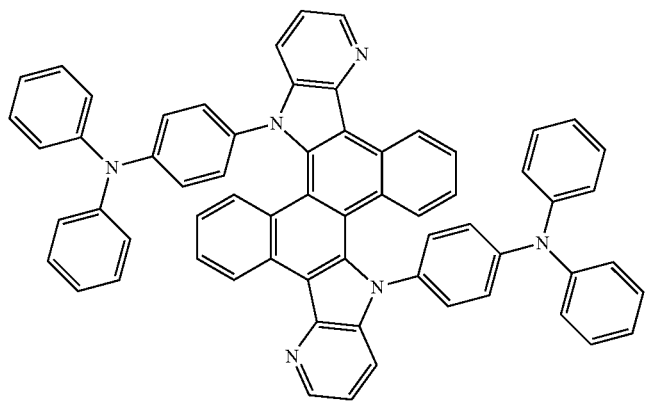

41

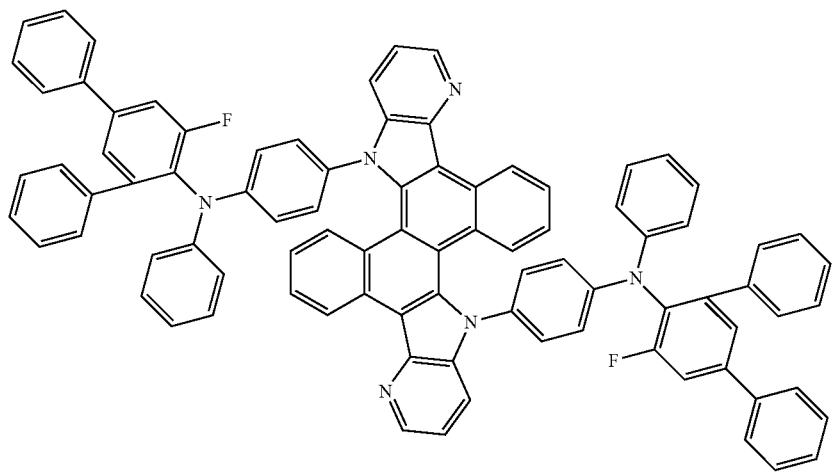

11. An organic light-emitting device comprising:
a first electrode;
a second electrode; and
an organic layer disposed between the first electrode and the second electrode, the organic layer comprising a first layer comprising the heterocyclic compound of claim 1.

12. The organic light-emitting device of claim 11, wherein the first layer comprises a hole injection layer, a hole transport layer, a functional layer having both hole injection and hole transport capabilities, an electron injection layer, an electron transport layer, or a functional layer having both electron injection and electron transport capabilities.

13. The organic light-emitting device of claim 11, wherein the first layer comprises an emission layer, and the heterocyclic compound is used as a host or dopant for a fluorescent or phosphorescent device.

14. The organic light-emitting device of claim 11, wherein the organic layer comprises an emission layer, a hole transport layer, and an electron transport layer, the first layer is the electron transport layer, the hole transport layer, or the electron transport layer, and the emission layer further comprises an anthracene compound, an arylamine compound, or a styryl compound.

15. The organic light-emitting device of claim 11, wherein the organic layer comprises an emission layer, a hole transport layer, and an electron transport layer, the first layer is the electron transport layer, the hole transport layer, or the electron transport layer, and the emission layer comprises red, green, blue, and white emission layers, one of which comprises a phosphorescent compound.

16. The organic light-emitting device of claim 11, wherein the organic layer further comprises a hole injection layer, a hole transport layer, a functional layer having both hole injection and hole transport capabilities, an emission layer, a hole blocking layer, an electron transport layer, an electron injection layer, or a combination of at least two thereof.

17. The organic light-emitting device of claim 16, wherein at least one of the hole injection layer, the hole transport layer, and the functional layer having hole injection and hole transport capabilities further comprises a charge generating material.

18. The organic light-emitting device of claim 16, wherein the emission layer comprises a host and a dopant, the dopant comprising a fluorescent dopant or a phosphorescent dopant.

19. The organic light-emitting device of claim 11, wherein the first layer comprising the heterocyclic compound is formed utilizing a wet process.

20. A flat panel display device comprising:
an organic light-emitting device, the organic light-emitting device comprising:
a first electrode;
a second electrode; and
an organic layer disposed between the first electrode and the second electrode, the organic layer comprising a first layer comprising the heterocyclic compound of claim 1, wherein the first electrode of the organic light-emitting device is configured to be electrically connected to a source electrode or a drain electrode of a thin-film transistor.

* * * * *